(12) United States Patent
Zilles et al.

(10) Patent No.: US 9,651,490 B2
(45) Date of Patent: May 16, 2017

(54) AMINE-SUBSTITUTED TRICYCLIC FLUORESCENT DYES

(75) Inventors: Alexander Zilles, Kreuztal (DE);
Karl-Heinz Drexhage, Siegen (DE);
Norbert Uwe Kemnitzer, Netphen (DE); Jutta Arden-Jacob, Zirndorf (DE); Monika Hamers-Schneider, Freudenberg (DE)

(73) Assignee: ATTO-TEC GMBH, Siegen (DE)

( * ) Notice: Subject to any disclaimer, the term of this patent is extended or adjusted under 35 U.S.C. 154(b) by 238 days.

(21) Appl. No.: 13/880,119

(22) PCT Filed: Oct. 18, 2011

(86) PCT No.: PCT/EP2011/068187
§ 371 (c)(1),
(2), (4) Date: Apr. 18, 2013

(87) PCT Pub. No.: WO2012/052435
PCT Pub. Date: Apr. 26, 2012

(65) Prior Publication Data
US 2013/0224871 A1    Aug. 29, 2013

(30) Foreign Application Priority Data
Oct. 19, 2010 (DE) .................. 10 2010 042 634

(51) Int. Cl.
*G01N 21/64* (2006.01)
*C09B 11/28* (2006.01)
*G01N 33/58* (2006.01)

(52) U.S. Cl.
CPC .......... *G01N 21/6428* (2013.01); *C09B 11/28* (2013.01); *G01N 33/582* (2013.01); *Y10T 436/143333* (2015.01)

(58) Field of Classification Search
CPC .......... C09B 11/28; Y10T 436/143333; G01N 21/6428; G01N 33/582
(Continued)

(56) References Cited

U.S. PATENT DOCUMENTS 2,073,086 A    3/1937 Winter et al.
4,320,940 A    3/1982 Mueller et al.
(Continued)

FOREIGN PATENT DOCUMENTS

DE    65739      11/1892
DE    3322945    1/1985
(Continued)

OTHER PUBLICATIONS

Ahn et al., "Combinatorial Rosamine Library and Application to in Vivo Glutathione Probe", Journal of the American Chemistry Society, vol. 129, No. 15, Apr. 2007, pp. 4510-4511.
(Continued)

*Primary Examiner* — Rebecca M Fritchman
(74) *Attorney, Agent, or Firm* — Kilpatrick Townsend & Stockton LLP

(57) ABSTRACT

The present invention relates to polycyclic compounds of the general formula (I) which are distinguished by an amine substituent $NR^6R^7$ on the central carbon atom of the chromophore, to processes for their preparation, and to the use thereof for the determination of analytes.

34 Claims, 10 Drawing Sheets

AZ 285

(58) Field of Classification Search
USPC .................................................. 436/86, 94
See application file for complete search history.

(56) References Cited

U.S. PATENT DOCUMENTS

| 5,851,621 | A | 12/1998 | Wolleb et al. |
| 6,828,159 | B1 | 12/2004 | Drexhage et al. |
| 2006/0211029 | A1* | 9/2006 | Mao et al. ............ 435/6 |
| 2010/0280246 | A1 | 11/2010 | Lee et al. |

FOREIGN PATENT DOCUMENTS

| DE | 19919119 | 11/2000 |
| DE | 69736434 | 3/2007 |
| EP | 0805441 | 11/1997 |
| GB | 420743 | 11/1934 |
| JP | 2006004736 | 1/2006 |
| WO | 0244416 | 6/2002 |
| WO | 03007296 | 1/2003 |
| WO | 2010033011 | 3/2010 |

OTHER PUBLICATIONS

Debray et al., "Synthesis and evaluation of fused bispyrimidinoacridines as novel pentacyclic analogues of quadruplex-binder BRACO-19", Org. Biomol. Chem., vol. 7, 2009, pp. 5219-5228.
Martins et al., "Structure-based design of benzylamino-acridine compounds as G-quadruplex DNA telomere targeting agents", Bioorganic & Medicinal Chemistry Letters, vol. 17, No. 8, Mar. 2007, pp. 2293-2298.
Mizuki et al., "Fluorescence enhancement of bis-acridine orange peptide, BAO, upon binding to double stranded DNA", Organic & Biomolecular Chemistry, vol. 3, 2005, pp. 578-580.
International Search Report and Written Opinion dated Jan. 12, 2012 in PCT Application No. PCT/EP2011/068187.
Shi et al., "Xanthenes: Flourone Derivatives II", Tetrahedron Letter, vol. 34, No. 38, 1993, pp. 6013-6016.
Wu et al., "Fluorescent Amino- and Thiopyronin Dyes", Organic Letters, American Chemical Society, US, vol. 10, No. 9, Jan. 2008, pp. 1779-1782.

* cited by examiner

AZ 277

AZ 293

AZ 111

AZ 115

AMINE-SUBSTITUTED TRICYCLIC FLUORESCENT DYES

PRIOR RELATED APPLICATIONS

This application is a National Phase application of International Application No. PCT/EP2011/068187 filed Oct. 18, 2011, which claims priority to DE 102010042634.2 filed Oct. 19, 2010, each of which is incorporated herein by reference in its entirety.

The present invention relates to polycyclic compounds of the general formula (I) which are distinguished by an amine substituent $NR^6R^7$ on the central carbon atom of the chromophore, to processes for their preparation, and to the use thereof for the determination of analytes.

In chemical, medical and biological analysis, organic dyes are used in many different ways as labelling and detection groups. Fluorescent dyes in particular have recently gained great practical importance and have almost completely displaced other earlier processes, which use radioactive isotopes, for example.

Despite the availability of a large number of different fluorescent dyes, it has hitherto not been possible satisfactorily to solve problems associated with background fluorescence, non-specific binding, instability under intensive laser radiation, etc. In particular, problems frequently arise owing to the small shift of the fluorescence band relative to the long-wave absorption band, which is characteristic of most dyes. It is typically only about 30 nm. This small shift, known as a Stokes shift, makes it difficult to separate the fluorescence signal cleanly from the scattered excitation light.

Furthermore, it is in many cases desirable or even necessary to distinguish a plurality of analytes from one another on excitation with the same light source on the basis of different fluorescence. Dyes required therefor with a large Stokes shift, that is to say a shift of the fluorescence band relative to the long-wave absorption band of >60 nm, and at the same time high fluorescence efficiency are almost entirely unknown.

The object underlying the present invention was accordingly to provide fluorescent dyes which have a large Stokes shift and high fluorescence efficiency and can be used for the qualitative or/and quantitative determination of analytes. Furthermore, it should be possible to produce those fluorescent dyes as simply and inexpensively as possible.

The object has been achieved according to the invention by polycyclic compounds of the general formula (I)

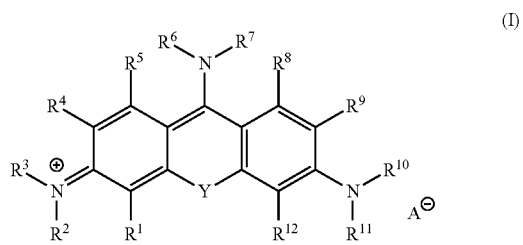

(I)

wherein $R^1$, $R^4$, $R^5$, $R^8$, $R^9$ and $R^{12}$ independently of one another denote hydrogen, halogen, CN, OH, O(alkyl), O(aryl), SH, S(alkyl), S(aryl), $NH_2$, NH(alkyl), NH(aryl), N(alkyl)$_2$, N(aryl)$_2$, $NO_2$, CHO, COOH, COO(alkyl), COO(aryl), $PO_3H_2$, $SO_3H$ or a hydrocarbon group having from 1 to 20 carbon atoms, wherein the hydrocarbon group optionally comprises one or more heteroatoms selected from the group consisting of N, O and S or/and one or more substituents selected from the group consisting of halogen, OH, O(alkyl), O(aryl), SH, S(alkyl), S(aryl), $NH_2$, NH(alkyl), NH(aryl), N(alkyl)$_2$, N(aryl)$_2$, $NO_2$, CHO, COOH, COO(alkyl), COO(aryl), $PO_3H_2$ and $SO_3H$, $R^2$, $R^3$, $R^{10}$ and $R^{11}$ independently of one another denote hydrogen or a hydrocarbon group having from 1 to 20 carbon atoms, wherein the hydrocarbon group optionally comprises one or more heteroatoms selected from the group consisting of N, O and S or/and one or more substituents selected from the group consisting of halogen, CN, OH, O(alkyl), O(aryl), SH, S(alkyl), S(aryl), $NH_2$, NH(alkyl), NH(aryl), N(alkyl)$_2$, N(aryl)$_2$, $NO_2$, CHO, COOH, COO(alkyl), COO(aryl), $PO_3H_2$ and $SO_3H$, $R^6$ and $R^7$ independently of one another denote hydrogen, $NR^{13}R^{14}$, a hydrocarbon group having from 1 to 20 carbon atoms, or an analyte molecule group, wherein $R^{13}$ and $R^{14}$ independently of one another denote hydrogen, halogen, CN, OH, O(alkyl), O(aryl), SH, S(alkyl), S(aryl), $NH_2$, NH(alkyl), NH(aryl), N(alkyl)$_2$, N(aryl)$_2$, $NO_2$, CHO, COOH, COO(alkyl), COO(aryl), $PO_3H_2$, $SO_3H$ or a hydrocarbon group having from 1 to 20 carbon atoms, and wherein the hydrocarbon group optionally comprises one or more heteroatoms selected from the group consisting of N, O and S or/and one or more substituents selected from the group consisting of halogen, CN, OH, O(alkyl), O(aryl), SH, S(alkyl), S(aryl), $NH_2$, NH(alkyl), NH(aryl), N(alkyl)$_2$, N(aryl)$_2$, $NO_2$, CHO, COOH, COO(alkyl), COO(aryl), $PO_3H_2$ and $SO_3H$, or $R^6$ and $R^7$, together with the N atom to which they are attached, form a 3- to 7-membered ring, wherein the ring can comprise one or more double bonds or/and one or more additional heteroatoms selected from the group consisting of N, O and S or/and one or more substituents selected from the group consisting of halogen, CN, OH, O(alkyl), O(aryl), SH, S(alkyl), S(aryl), $NH_2$, NH(alkyl), NH(aryl), N(alkyl)$_2$, N(aryl)$_2$, $NO_2$, CHO, COOH, COO(alkyl), COO(aryl), $PO_3H_2$, $SO_3H$ and a hydrocarbon group having from 1 to 20 carbon atoms or/and can be fused with one or more 3- to 7-membered rings, wherein the hydrocarbon group optionally comprises one or more heteroatoms selected from the group consisting of N, O and S or/and one or more substituents selected from the group consisting of halogen, CN, OH, O(alkyl), O(aryl), SH, S(alkyl), S(aryl), $NH_2$, NH(alkyl), NH(aryl), N(alkyl)$_2$, N(aryl)$_2$, $NO_2$, CHO, COOH, COO(alkyl), COO(aryl), $PO_3H_2$ and $SO_3H$, Y denotes a group selected from $CR^{15}R^{16}$, $NR^{17}$, O, S and Se, wherein $R^{15}$, $R^{16}$ and $R^{17}$ independently of one another denote hydrogen, CN, COOH, COO(alkyl), COO(aryl), $PO_3H_2$, $SO_3H$ or a hydrocarbon group having from 1 to 20 carbon atoms, wherein the hydrocarbon group optionally comprises one or more heteroatoms selected from the group consisting of N, O and S or/and one or more substituents selected from the group consisting of halogen, CN, OH, O(alkyl), O(aryl), SH, S(alkyl), S(aryl), $NH_2$, NH(alkyl), NH(aryl), N(alkyl)$_2$, N(aryl)$_2$, $NO_2$, CHO, COOH, COO(alkyl), COO(aryl), $PO_3H_2$ and $SO_3H$, or $R^{15}$ and $R^{16}$, together with the carbon atom to which they are attached, form a 3- to 7-membered ring, wherein the ring can comprise one or more double bonds or/and one or more heteroatoms selected from the group consisting of N, O and S or/and one or more substituents selected from the group consisting of halogen, CN, OH, O(alkyl), O(aryl), SH, S(alkyl), S(aryl), $NH_2$, NH(alkyl), NH(aryl), N(alkyl)$_2$, N(aryl)$_2$, $NO_2$, CHO, COOH, COO(alkyl), COO(aryl), PO$_3$H$_2$, SO$_3$H and a hydrocarbon group having from 1 to 20 carbon atoms or/and can be fused with one or more 3- to 7-membered rings, wherein the hydrocarbon group optionally comprises one or more heteroatoms selected from the group consisting of N, O and S or/and one or more substituents selected from the group consisting of halogen, CN, OH, O(alkyl), O(aryl), SH, S(alkyl), S(aryl), NH$_2$, NH(alkyl), NH(aryl), N(alkyl)$_2$, N(aryl)$_2$, NO$_2$, CHO, COOH, COO(alkyl), COO(aryl), PO$_3$H$_2$ and SO$_3$H, and A$^-$ denotes an anion, or wherein R$^1$ and R$^2$, R$^3$ and R$^4$, R$^9$ and R$^{10}$ or/and R$^{11}$ and R$^{12}$, together with the atoms to which they are attached, form a 5- or 6-membered ring, wherein the ring can comprise one or more double bonds or/and one or more substituents selected from the group consisting of halogen, CN, OH, O(alkyl), O(aryl), SH, S(alkyl), S(aryl), NH$_2$, NH(alkyl), NH(aryl), N(alkyl)$_2$, N(aryl)$_2$, NO$_2$, CHO, COOH, COO(alkyl), COO(aryl), PO$_3$H$_2$, SO$_3$H and a hydrocarbon group having from 1 to 20 carbon atoms, wherein the hydrocarbon group optionally comprises one or more heteroatoms selected from the group consisting of N, O and S or/and one or more substituents selected from the group consisting of halogen, CN, OH, O(alkyl), O(aryl), SH, S(alkyl), S(aryl), NH$_2$, NH(alkyl), NH(aryl), N(alkyl)$_2$, N(aryl)$_2$, NO$_2$, CHO, COOH, COO(alkyl), COO(aryl), PO$_3$H$_2$ and SO$_3$H.

The expression "hydrocarbon group" as used within the context of the present application includes a saturated or unsaturated hydrocarbon radical which can be linear, branched or cyclic and has a bond valence at any one of the 1 to 20 carbon atoms. Examples of hydrocarbon groups within the scope of the present invention include alkyl, cycloalkyl, alkenyl, alkynyl and aryl. If the hydrocarbon group comprises one or more heteroatoms selected from the group consisting of N, O and S, the hydrocarbon group can additionally be in the form of heteroaryl.

The term 'alkyl' as used within the context of the present application refers to a saturated, linear or branched hydrocarbon radical having from 1 to 20 carbon atoms which has a bond valence at any one of the 1 to 20 carbon atoms. Preferably, alkyl represents a hydrocarbon radical having from 1 to 12 carbon atoms, more preferably having from 1 to 6 carbon atoms. Particularly preferred alkyls include methyl, ethyl, n-propyl, isopropyl, n-butyl, isobutyl, sec-butyl and tert-butyl.

The term "cycloalkyl" as used within the context of the present application refers to a saturated or unsaturated, cyclic hydrocarbon radical having from 3 to 20 carbon atoms which has a bond valence at any one of the 3 to 20 carbon atoms. Preferably, cycloalkyl represents a cyclic hydrocarbon radical having from 3 to 12 carbon atoms, more preferably having from 3 to 8 carbon atoms. Particularly preferred cycloalkyls include cyclopropyl, cyclobutyl, cyclopentyl, cyclohexyl, cycloheptyl and cyclooctyl.

The term "alkenyl" as used within the context of the present application refers to an unsaturated, linear or branched hydrocarbon radical having from 2 to 20 carbon atoms which has a bond valence at any one of the 2 to 20 carbon atoms and at least one double bond. Preferably, alkenyl represents a hydrocarbon radical having from 2 to 12 carbon atoms, more preferably having from 2 to 6 carbon atoms. Particularly preferred alkenyls include ethenyl, propenyl and butenyl.

The term "alkynyl" as used within the context of the present application refers to an unsaturated, linear or branched hydrocarbon radical having from 2 to 20 carbon atoms which has a bond valence at any one of the 2 to 20 carbon atoms and at least one triple bond. Preferably, alkynyl represents a hydrocarbon radical having from 2 to 12 carbon atoms, more preferably having from 2 to 6 carbon atoms. Particularly preferred alkynyls include ethynyl, propynyl and butynyl.

The term "aryl" as used within the context of the present application refers to an aromatic ring system having from 3 to 20 ring atoms, more preferably having from 6 to 14 ring atoms, which contains solely carbon atoms as ring atoms and has a bond valence at any carbon atom of the 3 to 20 ring-forming atoms. Preferred aryls include phenyl, naphthyl, anthracenyl and phenanthrenyl.

The term "heteroaryl" as used within the context of the present application refers to an aromatic ring system having from 3 to 20 ring atoms, more preferably having from 5 to 14 ring atoms, which contains as ring atoms, in addition to carbon atoms, at least one heteroatom selected from the group consisting of N, O and S and has a bond valence at any carbon atom or nitrogen atom of the 3 to 20 ring-forming atoms. Preferred heteroaryls include furanyl, imidazolyl, isothiazolyl, isoxazolyl, oxadiazolyl, oxazolyl, pyrazolyl, pyrrolyl, tetrazolyl, thiadiazolyl, thiazolyl, thienyl, triazolyl, pyrazinyl, pyridazinyl, pyridyl, pyrimidinyl and triazinyl.

The term "halogen" as used within the context of the present application includes fluorine, chlorine, bromine and iodine.

The expression "analyte molecule group" as used within the context of the present application refers to the radical Z of an analyte molecule, which can be represented by the general formula Z—NH$_2$ and in that respect contains at least one free amino group for forming a covalent bond with a suitable reaction partner. In a preferred embodiment of the invention, the analyte molecule is a biomolecule, in particular a biomolecule selected from the group consisting of a peptide, a polypeptide, a protein, a nucleotide, a polynucleotide, a nucleoside, a nucleic acid, a nucleic acid analogue and a hapten.

In the polycyclic compounds of the general formula (I) according to the invention, R$^1$ and R$^2$, R$^3$ and R$^4$, R$^9$ and R$^{10}$ or/and R$^{11}$ and R$^{12}$, together with the atoms to which they are attached, form in a preferred embodiment a 5- or 6-membered ring, 6-membered rings being more preferred. The at least one 5- or 6-membered ring can comprise one or more double bonds or/and one or more substituents, for example 1, 2, 3 or 4 substituents, which can themselves be identical or different. The fluorescence of such compounds is particularly efficient and exhibits only slight dependence on temperature and environmental influences.

If the at least one 5- or 6-membered ring comprises one or more substituents, the substituents are selected from the group consisting of halogen, CN, OH, O(alkyl), O(aryl), SH, S(alkyl), S(aryl), NH$_2$, NH(alkyl), NH(aryl), N(alkyl)$_2$, N(aryl)$_2$, NO$_2$, CHO, COOH, COO(alkyl), COO(aryl), PO$_3$H$_2$, SO$_3$H and a hydrocarbon group having from 1 to 20 carbon atoms, wherein the hydrocarbon group optionally comprises one or more heteroatoms selected from the group consisting of N, O and S or/and one or more substituents selected from the group consisting of halogen, CN, OH, O(alkyl), O(aryl), SH, S(alkyl), S(aryl), NH$_2$, NH(alkyl), NH(aryl), N(alkyl)$_2$, N(aryl)$_2$, NO$_2$, CHO, COOH, COO(alkyl), COO(aryl), PO$_3$H$_2$ and SO$_3$H.

Used particularly preferably as substituents of the at least one 5- or 6-membered ring are hydrocarbon groups having from 1 to 20 carbon atoms, in particular alkyl groups having from 1 to 6 carbon atoms, wherein the hydrocarbon groups in the case of a substitution preferably comprise one or more substituents selected from the group consisting of COOH, COO(alkyl), COO(aryl) and SO$_3$H.

In a further preferred embodiment of the invention, the substituents R$^2$, R$^3$, R$^{10}$ or/and R$^{11}$ in the polycyclic compounds of the general formula (I) represent a hydrocarbon group having from 1 to 20 carbon atoms, wherein the hydrocarbon group optionally comprises one or more substituents selected from the group consisting of halogen, CN, OH, O(alkyl), O(aryl), SH, S(alkyl), S(aryl), NH$_2$, NH(alkyl), NH(aryl), N(alkyl)$_2$, N(aryl)$_2$, NO$_2$, CHO, COOH, COO(alkyl), COO(aryl), PO$_3$H$_2$ and SO$_3$H. Particularly preferably, the hydrocarbon group is an alkyl group having from 1 to 6 carbon atoms, in particular methyl or ethyl.

In a further preferred embodiment of the invention, at least two radicals selected from the group consisting of R$^5$, R$^8$ and R$^{12}$, in particular R$^5$ and R$^8$, denote hydrogen. Particularly preferably, however, polycyclic compounds of the general formula (I) are used according to the invention, wherein R$^5$, R$^8$ and R$^{12}$ each represents hydrogen.

The polycyclic compounds of the general formula (I) according to the invention necessarily comprise a functional group NR$^6$R$^7$. Preferably, R$^6$ and R$^7$ independently of one another denote hydrogen or a hydrocarbon group having from 1 to 20 carbon atoms, wherein the hydrocarbon group optionally comprises one or more substituents selected from the group consisting of halogen, CN, OH, O(alkyl), O(aryl), SH, S(alkyl), S(aryl), NH$_2$, NH(alkyl), NH(aryl), N(alkyl)$_2$, N(aryl)$_2$, NO$_2$, CHO, COOH, COO(alkyl), COO(aryl), PO$_3$H$_2$ and SO$_3$H. More preferably, R$^6$ and R$^7$ do not simultaneously represent hydrogen.

Yet more preferably, at least one of the substituents R$^6$ and R$^7$, that is to say R$^6$ or/and R$^7$, represents a hydrocarbon group having from 1 to 20 carbon atoms, in particular an alkyl group having from 1 to 6 carbon atoms or an aryl group having from 6 to 14 ring atoms, wherein the hydrocarbon group in the case of a substitution preferably comprises one or more substituents selected from the group consisting of halogen, OH, SH, NH$_2$, COOH, COO(alkyl), COO(aryl) and SO$_3$H, in particular one or more substituents selected from the group consisting of OH, NH$_2$, COOH and SO$_3$H. Particularly preferably, one of the substituents R$^6$ and R$^7$ denotes a hydrogen atom while the other substituent represents the above-defined hydrocarbon group having from 1 to 20 carbon atoms.

In the polycyclic compounds of the general formula (I) according to the invention, Y denotes a group selected from CR$^{15}$R$^{16}$, NR$^{17}$, O, S and Se, with preference being given to CR$^{15}$SR$^{16}$, O and S. More preferably, Y denotes a group selected from CR$^{15}$R$^{16}$ and O, most preferably CR$^{15}$R$^{16}$. If Y is represented by the group CR$^{15}$R$^{16}$, at least one of the radicals R$^{15}$ and R$^{16}$ preferably represents a hydrocarbon group having from 1 to 20 carbon atoms, preferably an alkyl group having from 1 to 6 carbon atoms, more preferably methyl or ethyl.

Table 1 shows examples of particularly preferred polycyclic compounds of the general formula (I) having a carbopyronine structure.

TABLE 1

| Compound | Structure | $\lambda_{abs}$ [nm] | $\lambda_{fl}$ [nm] | $\eta_{fl}$ [%] | Stokes Shift [nm] |
|---|---|---|---|---|---|
| 1 AZ 274 | | 472 EtOH | 586 EtOH | 75 EtOH | 114 EtOH |
| 2 AZ 279 | | 460 EtOH 453 PBS | 580 EtOH 606 PBS | 68 EtOH 34 PBS | 120 EtOH 153 PBS |
| 3 AZ 281 | | 485 EtOH 484 PBS | 617 EtOH 650 PBS | 67 EtOH 31 PBS | 132 EtOH 166 PBS |

TABLE 1-continued
| Compound | Structure | $\lambda_{abs}$ [nm] | $\lambda_{fl}$ [nm] | $\eta_{fl}$ [%] | Stokes Shift [nm] |
|---|---|---|---|---|---|
| 4 AZ 285 | 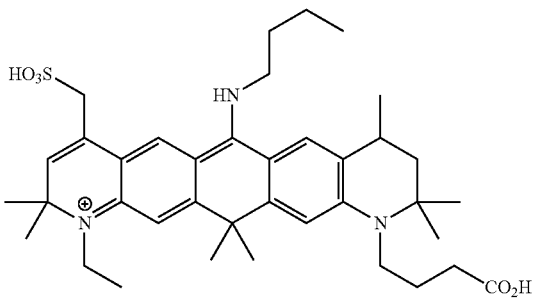 [SMILES: CCCCNC1=c2cc3c(cc2C(C)(C)c2cc4c(cc21)C(C)CC(C)(C)N4CCCC(=O)O)=[N+](CC)C(C)(C)C=C3CS(=O)(=O)O] | 484 EtOH 484 PBS | 623 EtOH 653 PBS | 65 EtOH 32 PBS | 139 EtOH 169 PBS |
| 5 AZ 286 | 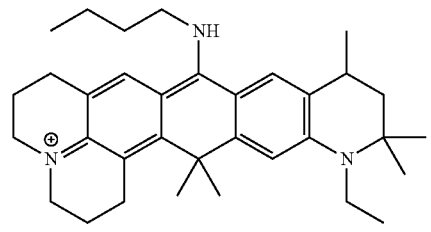 [SMILES: CCCCNC1=c2cc3c4c(c2C(C)(C)c2cc5c(cc21)C(C)CC(C)(C)N5CC)CCC[N+]=4CCC3] | 480 EtOH | 601 EtOH | 79 EtOH | 121 EtOH |
| 6 AZ 291 | 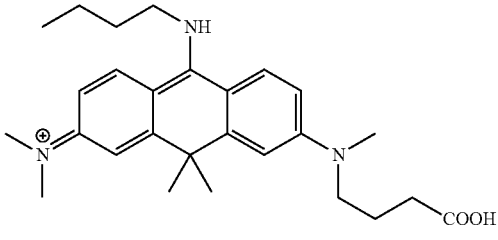 [SMILES: CCCCNC1=C2C=CC(=[N+](C)C)C=C2C(C)(C)c2cc(N(C)CCCC(=O)O)ccc21] | 465 EtOH 455 PBS | 579 EtOH 605 PBS | 65 EtOH | 114 EtOH 150 PBS |
| 7 AZ 292 | 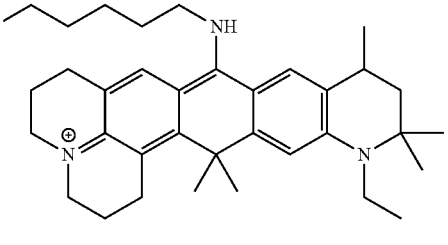 | 480 EtOH 476 PBS | 601 EtOH 618 PBS | 78 EtOH | 121 EtOH 142 PBS |
| 8 AZ 312 | 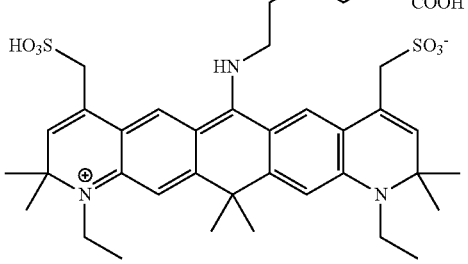 | 491 EtOH 490 PBS | 651 EtOH 670 PBS | 61 EtOH 26 PBS | 160 EtOH 180 PBS |
| 9 AZ 315 | 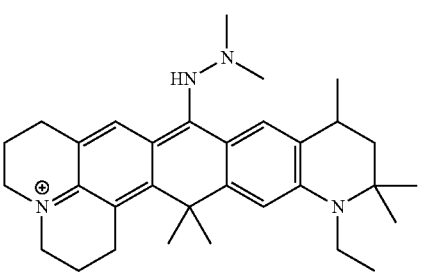 [SMILES: CCN1c2cc3c(cc2C(C)CC1(C)C)C(NN(C)C)=c1cc2c4c(c1C3(C)C)CCC[N+]=4CCC2] | 492 EtOH | 605 EtOH | 50 EtOH | 113 EtOH |

TABLE 1-continued
| Compound | Structure | λ$_{abs}$ [nm] | λ$_{fl}$ [nm] | η$_{fl}$ [%] | Stokes Shift [nm] |
|---|---|---|---|---|---|
| 10 AZ 317 | 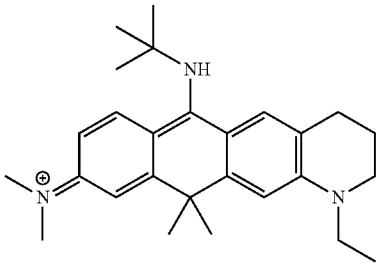 [SMILES: CCN1CCCc2cc3c(cc21)C(C)(C)C1=CC(=[N+](C)C)C=CC1=C3NC(C)(C)C] | 493 EtOH | 644 EtOH | 63 EtOH | 151 EtOH |
| 11 AZ 322 | 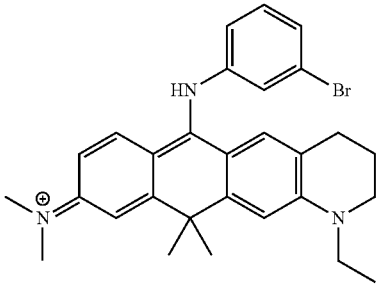 [SMILES: CCN1CCCc2cc3c(cc21)C(C)(C)C1=CC(=[N+](C)C)C=CC1=C3Nc1cccc(Br)c1] | 523 EtOH | 644 EtOH | 1 EtOH | 121 EtOH |
| 12 AZ 323 | 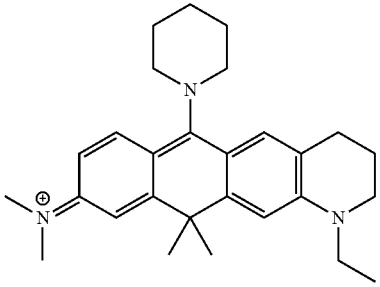 [SMILES: CCN1CCCc2cc3c(cc21)C(C)(C)C1=CC(=[N+](C)C)C=CC1=C3N1CCCCC1] | 475 EtOH | 588 EtOH | 8 EtOH | 113 EtOH |
| 13 AZ 324 | 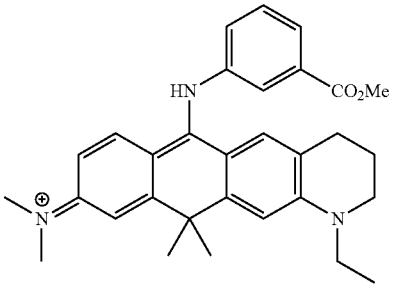 [SMILES: CCN1CCCc2cc3c(cc21)C(C)(C)C1=CC(=[N+](C)C)C=CC1=C3Nc1cccc(C(=O)OC)c1] | 520 EtOH | 641 EtOH | 2 EtOH | 121 EtOH |
| 14 AZ 327 | 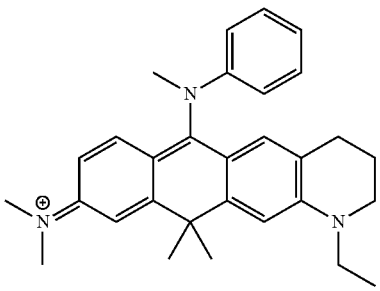 [SMILES: CCN1CCCc2cc3c(cc21)C(C)(C)C1=CC(=[N+](C)C)C=CC1=C3N(C)c1ccccc1] | 629 EtOH | | <0.1 EtOH | |

TABLE 1-continued

| Compound | Structure | $\lambda_{abs}$ [nm] | $\lambda_{fl}$ [nm] | $\eta_{fl}$ [%] | Stokes Shift [nm] |
|---|---|---|---|---|---|
| 15 AZ 329 | 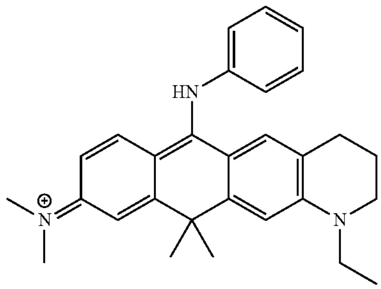 [SMILES: CCN1CCCc2cc3c(cc21)C(C)(C)C1=CC(=[N+](C)C)C=CC1=C3Nc1ccccc1] | 507 EtOH | 620 EtOH | <1 EtOH | 113 EtOH |
| 16 AZ 330 | 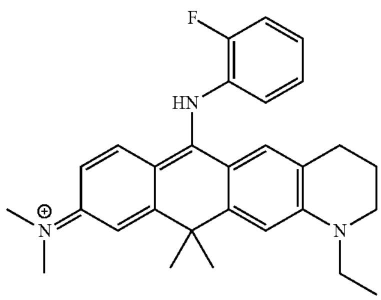 [SMILES: CCN1CCCc2cc3c(cc21)C(C)(C)C1=CC(=[N+](C)C)C=CC1=C3Nc1ccccc1F] | 512 EtOH | 620 EtOH | 4 EtOH | 108 EtOH |
| 17 AZ 332 | 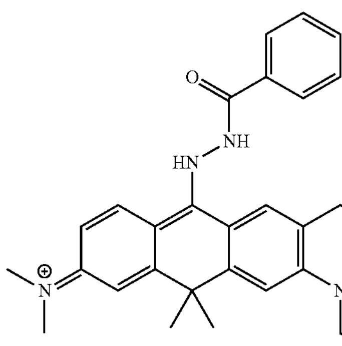 | 497 EtOH | 622 EtOH | 55 EtOH | 125 EtOH |
| 18 AZ 334 | 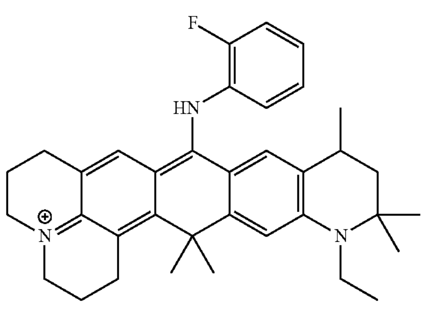 [SMILES: CCN1c2cc3c(cc2C(C)CC1(C)C)C(Nc1ccccc1F)=c1cc2c4c(c1C3(C)C)CCC[N+]=4CCC2] | 526 EtOH | 627 EtOH | 11 EtOH | 101 EtOH |

TABLE 1-continued

| Compound | Structure | $\lambda_{abs}$ [nm] | $\lambda_{fl}$ [nm] | $\eta_{fl}$ [%] | Stokes Shift [nm] |
|---|---|---|---|---|---|
| 19 AZ 336 | | 517 EtOH | 638 EtOH | 2 EtOH | 121 EtOH |
| 20 AZ 342 | | 484 EtOH | 603 EtOH | 78 EtOH | 119 EtOH |

Table 2 shows examples of particularly preferred polycyclic compounds of the general formula (I) having a rhodamine structure.

TABLE 2

| Compound | Structure | $\lambda_{abs}$ [nm] | $\lambda_{fl}$ [nm] | $\eta_{fl}$ [%] | Stokes Shift [nm] |
|---|---|---|---|---|---|
| 21 AZ 277 | | 456 EtOH | 555 EtOH | 82 EtOH | 99 EtOH |
| 22 AZ 278 | | 433 EtOH | 524 EtOH | 47 EtOH | 91 EtOH |
| 23 AZ 293 | | 434 EtOH | 524 EtOH | 48 EtOH | 90 EtOH |

TABLE 2-continued

| Compound | Structure | $\lambda_{abs}$ [nm] | $\lambda_{fl}$ [nm] | $\eta_{fl}$ [%] | Stokes Shift [nm] |
|---|---|---|---|---|---|
| 24 AZ 294 | | 459 EtOH 454 PBS | 555 EtOH 568 PBS | 80 EtOH 60 PBS | 96 EtOH 114 PBS |
| 25 AZ 313 | | 484 EtOH | 546 EtOH | | 62 EtOH |

Table 3 shows examples of further particularly preferred polycyclic compounds of the general formula (I) within the scope of the present invention.

TABLE 3

| Compound | Structure | $\lambda_{abs}$ [nm] | $\lambda_{fl}$ [nm] | $\eta_{fl}$ [%] | Stokes Shift [nm] |
|---|---|---|---|---|---|
| 26 AZ 307 | | 451 EtOH | 563 EtOH | 55 EtOH | 112 EtOH |
| 27 AZ 308 | | 432 EtOH | 506 EtOH | | 74 EtOH |

In a further aspect, the invention relates to a process for the preparation of a polycyclic compound of the general formula (I), wherein a polycyclic precursor compound of the general formula (II)

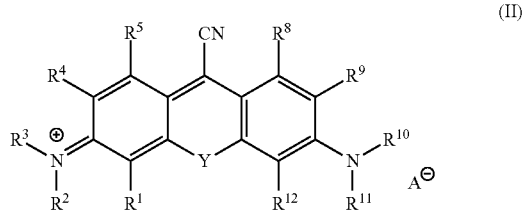
(II)

or a polycyclic precursor compound of the general formula (III)

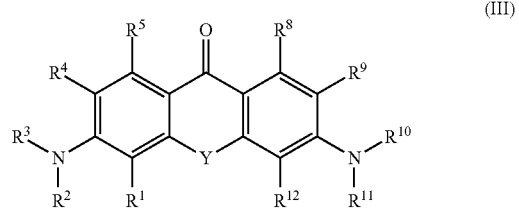
(III)

is reacted with a primary or secondary amine of the general formula $HNR^6R^7$ and $R^1$, $R^2$, $R^3$, $R^4$, $R^5$, $R^6$, $R^7$, $R^8$, $R^9$, $R^{10}$, $R^{11}$, $R^{12}$, Y and $A^-$ are as defined for the above-described polycyclic compounds of the general formula (I) according to the invention.

The preparation of the polycyclic compounds of the general formula (I) according to the invention is usually carried out in the presence of a solvent, in particular of a solvent selected from the group consisting of acetone, acetonitrile, chloroform, dichloromethane, dimethyl sulfoxide and N,N-dimethylformamide. If required, mixtures of the above-mentioned solvents can also be used.

In detail, for the preparation of the polycyclic compounds of the general formula (I), a primary or secondary amine of the general formula $HNR^6R^7$ is added to a polycyclic precursor compound of the general formula (II) or (III), for example in solution in a solvent as defined above, the reaction mixture is stirred at a temperature of usually at least 0° C., in particular at a temperature in the range of from 15° C. to 35° C., until the reaction is complete, and the reaction product is purified using methods known to the person skilled in the art.

In one embodiment, the preparation of the polycyclic compounds of the general formula (I), in particular when a polycyclic precursor compound of the general formula (III) is used as starting material, can additionally include an activation of the polycyclic precursor compound, which is usually carried out before the polycyclic precursor compound is brought into contact with the primary or secondary amine of the general formula $HNR^6R^7$. Any activating reagent that appears suitable to the person skilled in the art can in principle be used for the activation of the polycyclic precursor compounds of the general formula (II) or (III), preference being given to chemical activating reagents such as, for example, trifluoromethanesulfonic anhydride.

In yet a further aspect, the invention relates to polycyclic precursor compounds of the general formula (II)

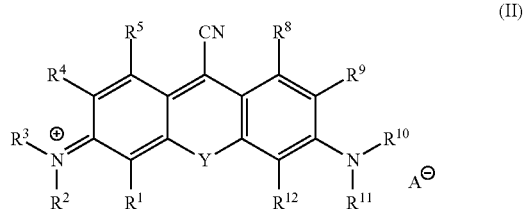
(II)

wherein $R^1$, $R^2$, $R^5$, $R^8$, $R^9$, $R^{10}$, $R^{11}$, $R^{12}$, Y and $A^-$ are as defined for the above-described polycyclic compounds of the general formula (I) according to the invention. With regard to preferred embodiments of the substituents contained in the polycyclic precursor compounds of the general formula (II), reference is made to the explanations given in connection with the polycyclic compounds of the general formula (I).

Table 4 shows examples of particularly preferred polycyclic precursor compounds of the general formula (II) with their absorption and fluorescence maxima (measured in ethanol).

TABLE 4

| Compound | Structure | $\lambda_{abs}$ [nm] | $\lambda_{fl}$ [nm] |
|---|---|---|---|
| 28 AZ 111 | 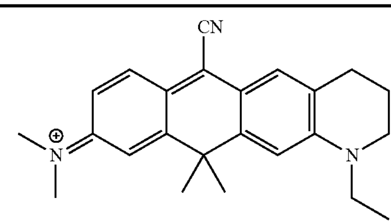 | 723 | 755 |
| 29 AZ 112 | 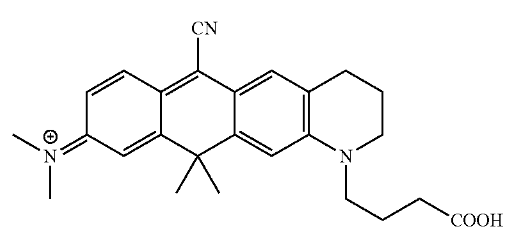 [SMILES: C[N+](C)=C1C=CC2=C(C#N)c3cc4c(cc3C(C)(C)C2=C1)N(CCCC(=O)O)CCC4] | 726 | 754 |

TABLE 4-continued

| Compound | Structure | $\lambda_{abs}$ [nm] | $\lambda_{fl}$ [nm] |
|---|---|---|---|
| 30 AZ 115 | | 710 | 742 |
| 31 AZ 144 | | 771 | 794 |
| 32 AZ 147 | | 801 | 830 |
| 33 AZ 284 | | 741 | 766 |
| 34 AZ 305 | | 666 | 690 |
| 35 AZ 306 | | 583 | 599 |

In yet a further aspect, the invention relates to a process for the preparation of a polycyclic precursor compound of the general formula (II), wherein a polycyclic precursor compound of the general formula (IV)

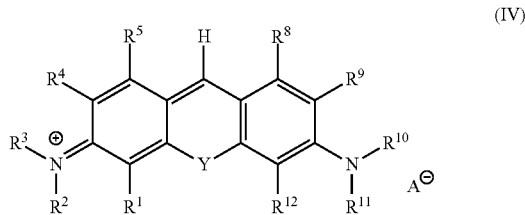

(IV)

is reacted with a tetraalkylammonium cyanide of the general formula N(alkyl)$_4$CN and an oxidising agent and $R^1$, $R^2$, $R^3$, $R^4$, $R^5$, $R^8$, $R^9$, $R^{10}$, $R^{11}$, $R^{12}$ and Y are as defined for the above-described polycyclic compounds of the general formula (I) according to the invention.

The preparation of the polycyclic precursor compounds of the general formula (II) according to the invention is preferably carried out in the presence of a solvent, in particular of a solvent selected from the group consisting of acetone, acetonitrile, chloroform, dichloromethane, dimethyl sulfoxide and N,N-dimethylformamide. If required, mixtures of the above-mentioned solvents can also be used.

In detail, for the preparation of the polycyclic precursor compounds of the general formula (II), a tetraalkylammonium cyanide of the general formula N(alkyl)$_4$CN and a suitable oxidising agent are added to a polycyclic precursor compound of the general formula (IV), for example in solution in a solvent as defined above, the reaction mixture is stirred at a temperature of usually at least 0° C., in particular at a temperature in the range of from 15° C. to 35° C., until the reaction is complete, and the reaction product is purified using methods known to the person skilled in the art.

The oxidising agent can in principle be any reagent that is able to effect oxidation to the chromophore. For the purposes of the present invention, chloranil has been found to be particularly advantageous, it being possible to use also other oxidising agents that appear suitable to the person skilled in the art, such as, for example, sodium periodate or lead dioxide.

In yet a further aspect, the invention relates to polycyclic precursor compounds of the general formula (III)

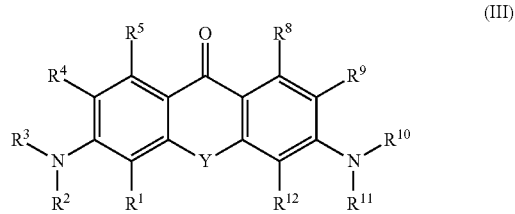

(III)

wherein $R^1$, $R^2$, $R^3$, $R^4$, $R^5$, $R^8$, $R^9$, $R^{10}$, $R^{11}$, $R^{12}$ and Y are as defined for the above-described polycyclic compounds of the general formula (I) according to the invention. With regard to preferred embodiments of the substituents contained in the polycyclic precursor compounds of the general formula (III), reference is made to the explanations given in connection with the polycyclic compounds of the general formula (I).

Table 5 shows examples of particularly preferred polycyclic precursor compounds of the general formula (III) with their absorption maxima (measured in ethanol).

TABLE 5

| Compound | Structure | $\lambda_{abs}$ [nm] |
|---|---|---|
| 36 AZ 35-A | 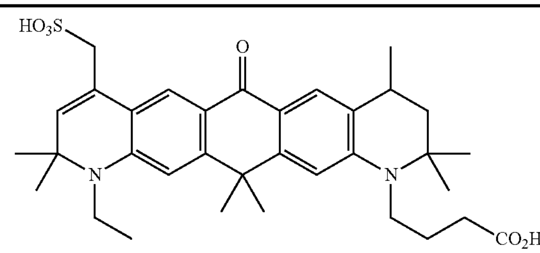 | 421 |
| 37 AZ 110-A | 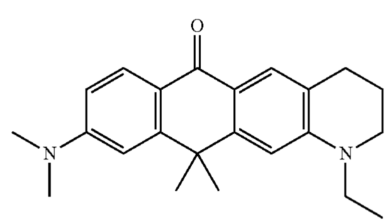 [SMILES: CCN1CCCc2cc3c(cc21)C(C)(C)c1cc(N(C)C)ccc1C3=O] | 400 |
| 38 AZ 124-A | 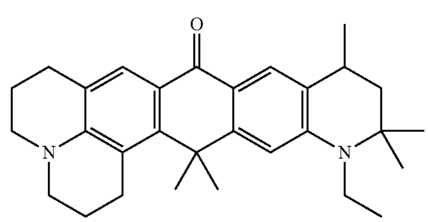 [SMILES: CCN1c2cc3c(cc2C(C)CC1(C)C)C(=O)c1cc2c4c(c1C3(C)C)CCCN4CCC2] | 409 |

TABLE 5-continued

| Compound | Structure | $\lambda_{abs}$ [nm] |
|---|---|---|
| 39 AZ 145-A | 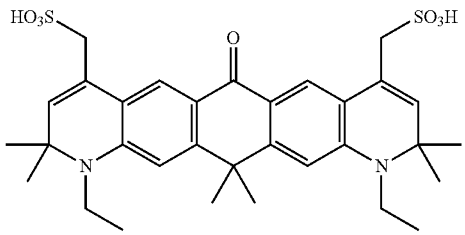 | 438 |
| 40 AZ 151-A | 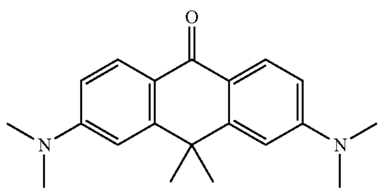 | 394 |
| 41 AZ 156-A | 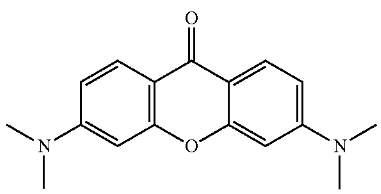 | 380 |
| 42 AZ 170-A | 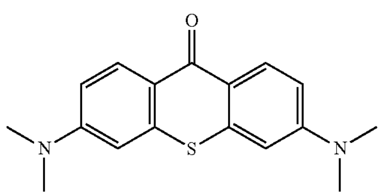 | 384 |
| 43 ATTO 495-A | 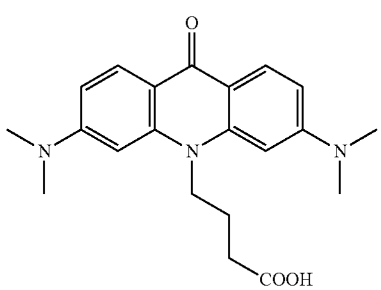 | 360 |
| 44 ATTO 610-A | 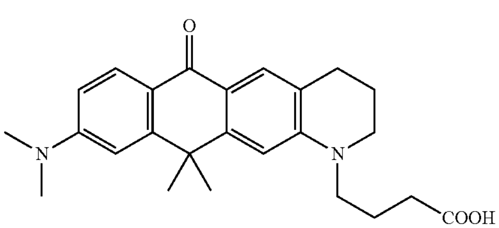 [SMILES: CN(C)c1ccc2c(c1)C(C)(C)c1cc3c(cc1C2=O)CCCN3CCCC(=O)O] | 401 |

In yet a further aspect, the invention relates to a process for the preparation of a polycyclic precursor compound of the general formula (III), wherein a polycyclic precursor compound of the general formula (IV)

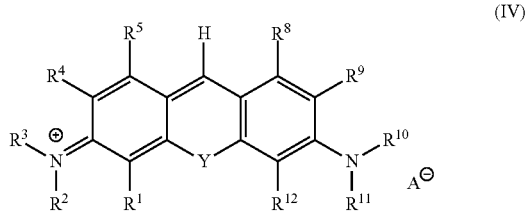

is reacted with an oxidising agent and $R^1$, $R^2$, $R^3$, $R^4$, $R^5$, $R^8$, $R^9$, $R^{10}$, $R^{11}$, $R^{12}$, Y and $A^-$ are as defined for the above-described polycyclic compounds of the general formula (I) according to the invention.

The preparation of the polycyclic precursor compounds of the general formula (III) according to the invention is preferably carried out in the presence of a solvent, in particular of a solvent selected from the group consisting of acetone, acetonitrile, chloroform, dichloromethane, dimethyl sulfoxide and N,N-dimethylformamide. If required, mixtures of the above-mentioned solvents can also be used.

In detail, for the preparation of the polycyclic precursor compounds of the general formula (III), an oxidising agent is added to a polycyclic precursor compound of the general formula (IV), for example in solution in a solvent as defined above, the reaction mixture is stirred at a temperature of usually at least 0° C., in particular at a temperature in the range of from 15° C. to 35° C., until the reaction is complete, and the reaction product is purified using methods known to the person skilled in the art.

The oxidising agent can in principle be any reagent that is able to effect a regioselective oxidation at the central carbon atom of the chromophore. For the purposes of the present invention, potassium permanganate has been found to be particularly advantageous, it being possible to use also other oxidising agents that appear suitable to the person skilled in the art.

Table 6 shows examples of particularly preferred polycyclic precursor compounds of the general formula (IV) with their absorption and fluorescence maxima (measured in ethanol).

TABLE 6

| Compound | Structure | $\lambda_{abs}$ [nm] | $\lambda_{fl}$ [nm] |
|---|---|---|---|
| 45 AZ 110 | 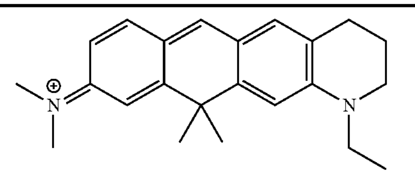 | 616 | 635 |
| 46 AZ 124 | 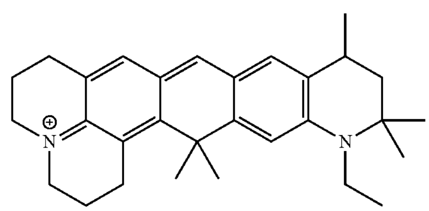 [SMILES: CCN1c2cc3c(cc2C(C)CC1(C)C)C=c1cc2c4c(c1C3(C)C)CCC[N+]=4CCC2] | 628 | 649 |
| 47 AZ 145 | 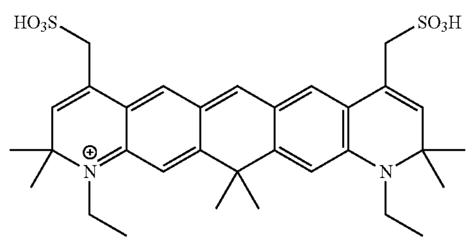 | 665 | 687 |
| 48 AZ 151 | 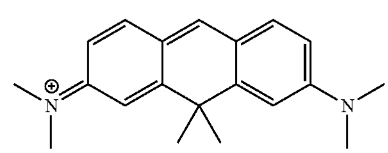 | 605 | 628 |
| 49 ATTO 610 | 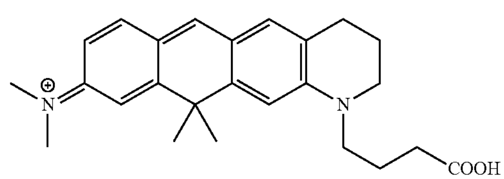 [SMILES: C[N+](C)=C1C=CC2=Cc3cc4c(cc3C(C)(C)C2=C1)N(CCCC(=O)O)CCC4] | 616 | 636 |

In yet a further aspect, the invention relates to the use of a polycyclic compound of the general formula (I) according to the invention or of a polycyclic precursor compound of the general formula (II) or (III) according to the invention for the qualitative or/and quantitative determination of an analyte in a sample, wherein the analyte can be any biological or chemical substance that can be detected photochemically. Preferred analytes within the scope of the present application are biomolecules, in particular peptides, polypeptides, proteins, nucleotides, polynucleotides, nucleosides, nucleic acids, nucleic acid analogues or happens.

The analyte can in principle come from any source, but it is preferably contained in a body fluid, such as, for example, whole blood, plasma, serum, lymph, bile, cerebrospinal fluid, extracellular tissue fluid, urine, saliva and sweat, in a waste-water sample or in a foodstuff. Preferably, however, the presence or/and the amount of an analyte in a sample of whole blood, plasma, serum or urine is determined by means of the polycyclic compounds or precursor compounds described herein.

An advantage of the polycyclic compounds of the general formula (I) and of the polycyclic precursor compounds of the general formulae (II) and (III) according to the invention is that, by varying the substituents, the physical and chemical properties of the compounds, such as, for example, the position of the absorption and fluorescence maxima, the solubility, the fluorescence quantum yield and the decay time, can be varied considerably and thus adapted to particular requirements. In that manner, it is possible, for example, to reduce or even avoid completely interference with disturbing substances in samples such as serum, blood or plasma.

In order to permit determination of the analyte, the polycyclic compounds or precursor compounds according to the invention contain, in addition to the grouping —$NR^6R^7$ that is necessarily present, preferably at least one functional group capable of covalent coupling, such as, for example, OH, SH, $NH_2$ or/and COOH. By way of that coupling group, which can be located at any desired position of the molecule, the compound in question can be coupled by means of known processes, for example by way of the intermediate of an N-hydroxysuccinimidyl ester, to a suitable carrier or/and to an analyte as is described above.

If the analyte can be represented by the general formula Z—$NH_2$ and accordingly comprises at least one free amino group, the analyte can also be reacted directly with a polycyclic precursor compound of the general formula (II) or (III). In that manner it is possible to prepare polycyclic compounds of the general formula (I) in which the grouping —$NR^6R^7$ comes directly from the analyte. In that case, it is not necessary for the polycyclic compounds or precursor compounds according to the invention to comprise an additional functional group capable of covalent coupling to the analyte.

If a carrier is used within the context of the determination of the analyte, the carrier can in principle consist of any material that appears suitable to the person skilled in the art and can be wetted by the sample to be tested. Examples of such carrier materials include, but are not limited to, porous glass, plastics, ion-exchange resins, dextrans, cellulose, cellulose derivatives or/and hydrophilic polymers.

In a preferred embodiment of the invention, however, the determination of the analyte provides for the analyte to be labelled by covalent bonding of a polycyclic compound of the general formula (I) or of a polycyclic precursor compound of the general formula (II) or (III) according to the invention to the analyte.

Table 7 shows examples of biological conjugates which can be obtained by coupling to particularly preferred polycyclic compounds of the general formula (I).

TABLE 7

| Compound | Structure | $\lambda_{abs}$ [nm] | $\lambda_{fl}$ [nm] | $\eta_{fl}$ [%] | Stokes Shift [nm] |
|---|---|---|---|---|---|
| 50 AZ 291-Streptavidin | 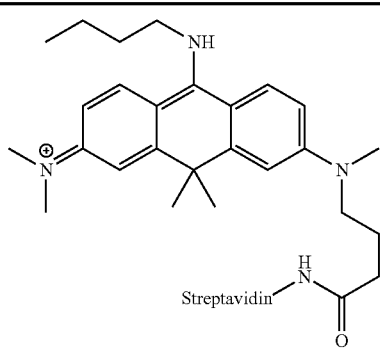 | 463 PBS | 592 PBS | 17 PBS | 129 PBS |
| 51 AZ 292-Streptavidin | 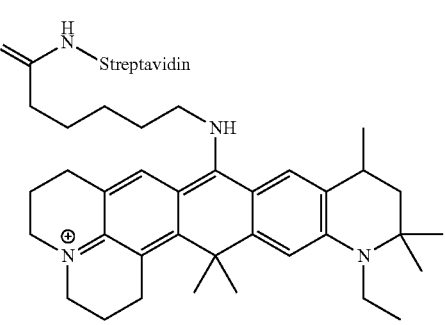 | 483 PBS | 618 PBS | 50 PBS | 135 PBS |

For the qualitative or/and quantitative determination of the analyte, in principle any method known from the prior art can be used, provided it generates a measurable signal which can be evaluated manually or using suitable means. Within the context of the present invention, optical detection methods are preferably used, which include, for example, the measurement of absorption, fluorescence, circular dichroism (CD), optical rotatory dispersion (ORD), refractometry, etc. Detection of the analyte is particularly preferably carried out by photometry or fluorometry.

A liquid test can be used to detect the analyte, wherein the compounds according to the invention are present, for example, in the form of a solution or as a suspension in an aqueous or non-aqueous liquid. In order to increase the solubility in aqueous liquids in particular, the polycyclic compounds or precursor compounds according to the invention can further comprise at least one functional group that increases water solubility, such as, for example, COOH or $SO_3H$, which functional group can be located at any desired position of the molecule. However, a dry test can also be used, the compounds according to the invention in that case being applied, for example, to a suitable carrier as is described above.

The invention will be explained in greater detail by the following figures and examples:

EXAMPLES

Figure 1:
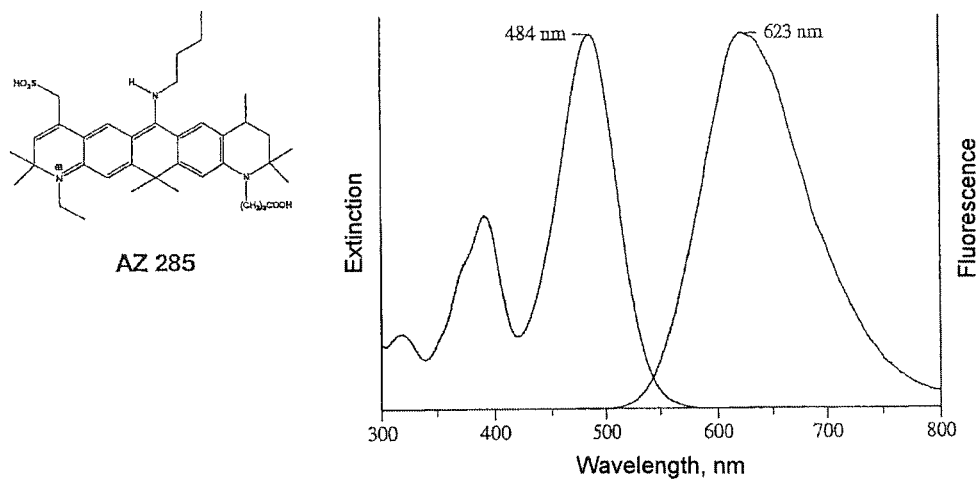
FIG. 1: Absorption and fluorescence spectrum of polycyclic compound 4 (AZ 285) in ethanol.
Figure 2:
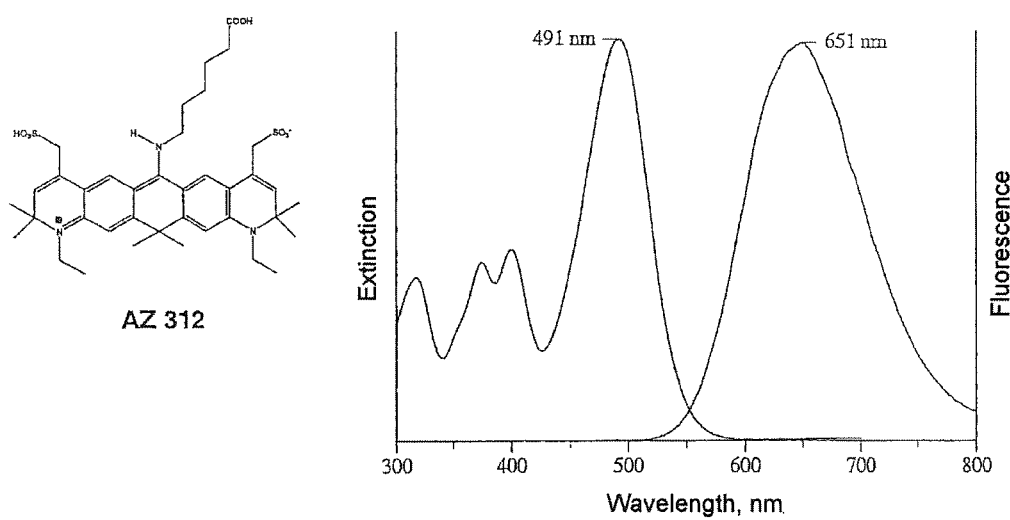
FIG. 2: Absorption and fluorescence spectrum of polycyclic compound 8 (AZ 312) in ethanol.
Figure 3:
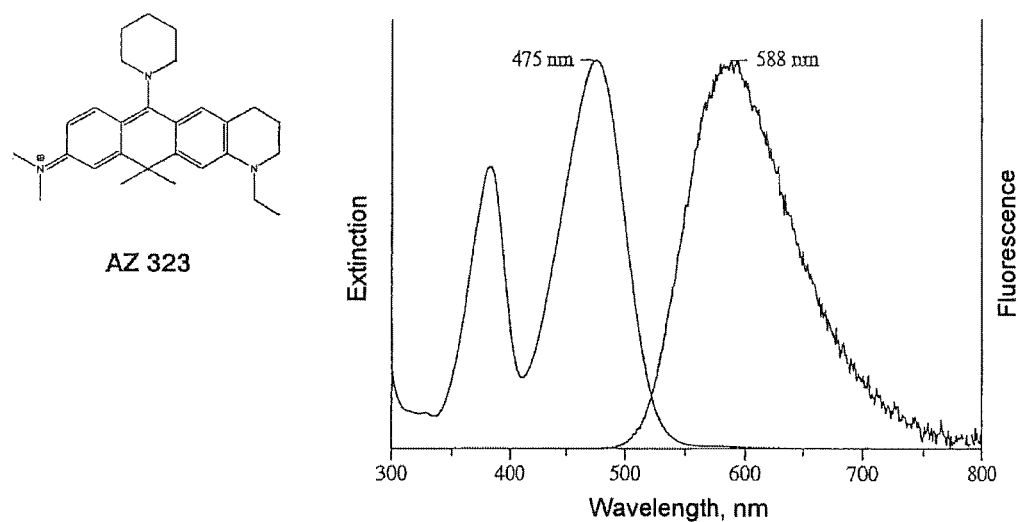
FIG. 3: Absorption and fluorescence spectrum of polycyclic compound 12 (AZ 323) in ethanol.
Figure 4:
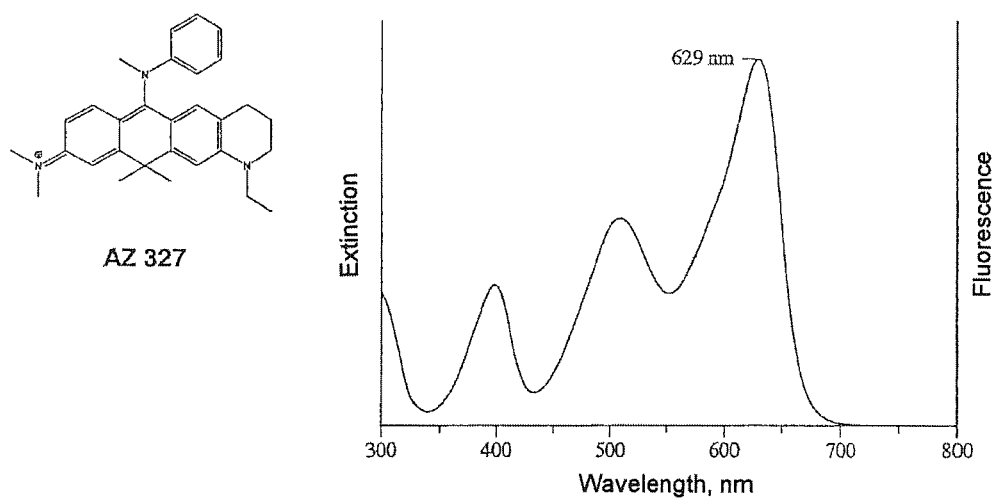
FIG. 4: Absorption spectrum of polycyclic compound 14 (AZ 327) in ethanol.
Figure 5:
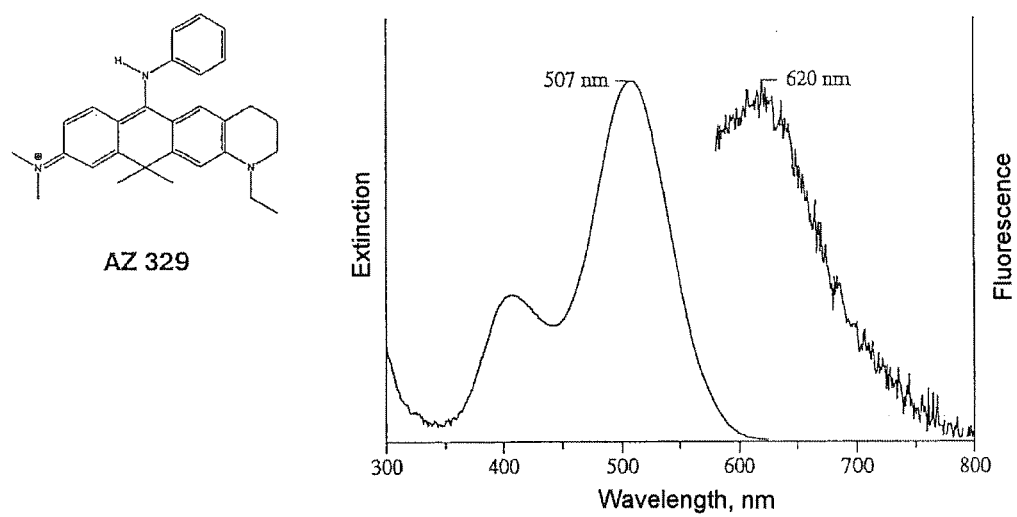
FIG. 5: Absorption and fluorescence spectrum of polycyclic compound 15 (AZ 329) in ethanol.
Figure 6:
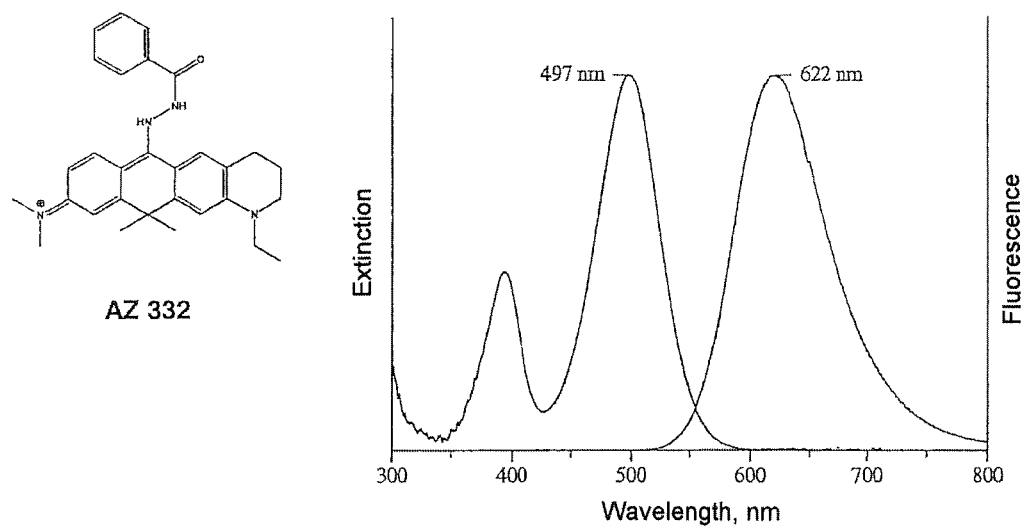
FIG. 6: Absorption and fluorescence spectrum of polycyclic compound 17 (AZ 332) in ethanol.
Figure 7:
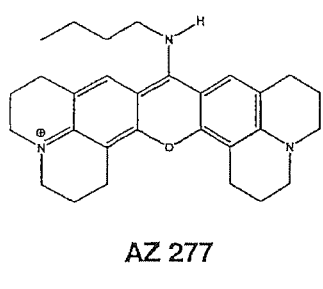
FIG. 7: Absorption and fluorescence spectrum of polycyclic compound 21 (AZ 277) in ethanol.
Figure 7:
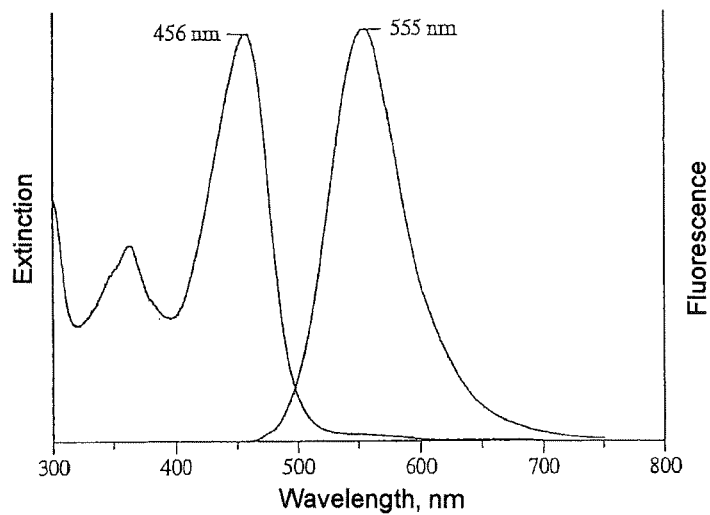
Figure 8:
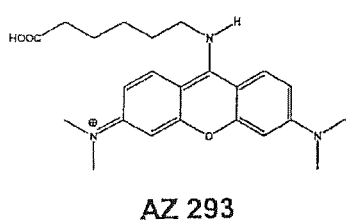
FIG. 8: Absorption and fluorescence spectrum of polycyclic compound 23 (AZ 293) in ethanol.
Figure 8:
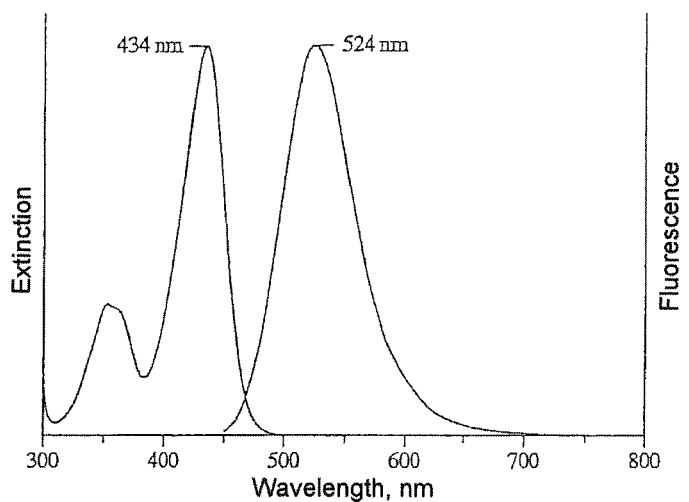
Figure 9:
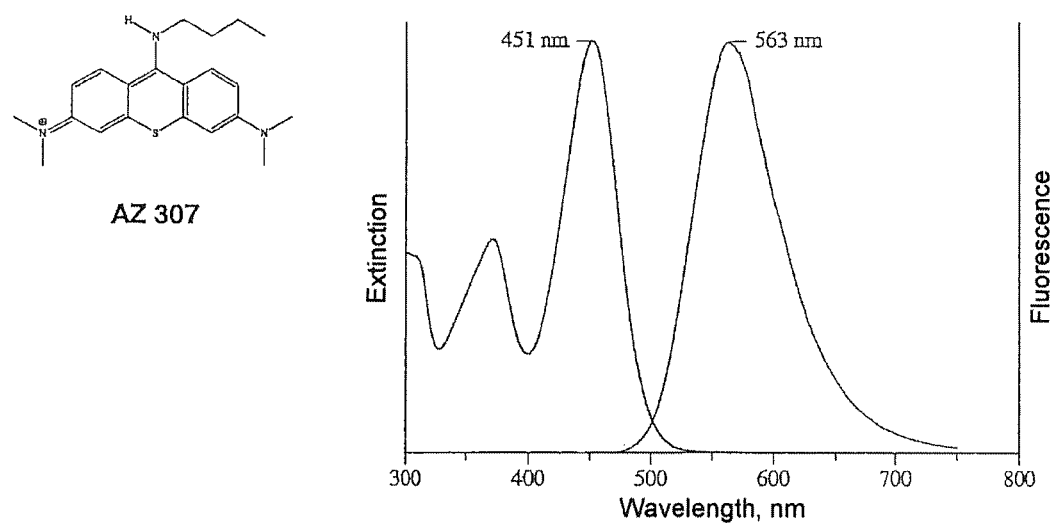
FIG. 9: Absorption and fluorescence spectrum of polycyclic compound 26 (AZ 307) in ethanol.
Figure 10:
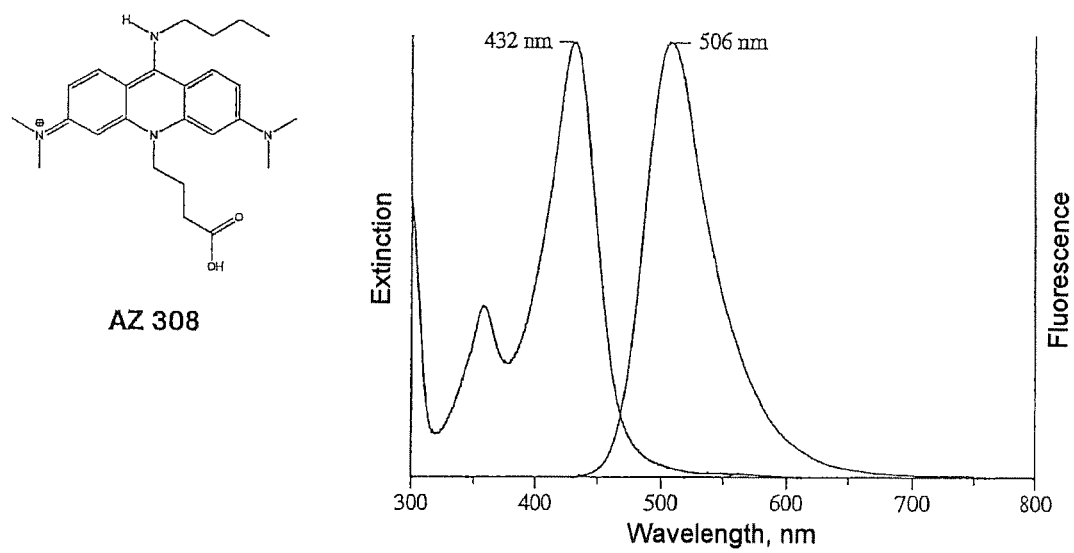
FIG. 10: Absorption and fluorescence spectrum of polycyclic compound 27 (AZ 308) in ethanol.
Figure 11:
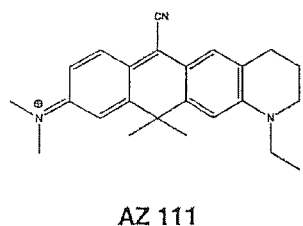
FIG. 11: Absorption and fluorescence spectrum of polycyclic compound 28 (AZ 111) in ethanol.
Figure 11:
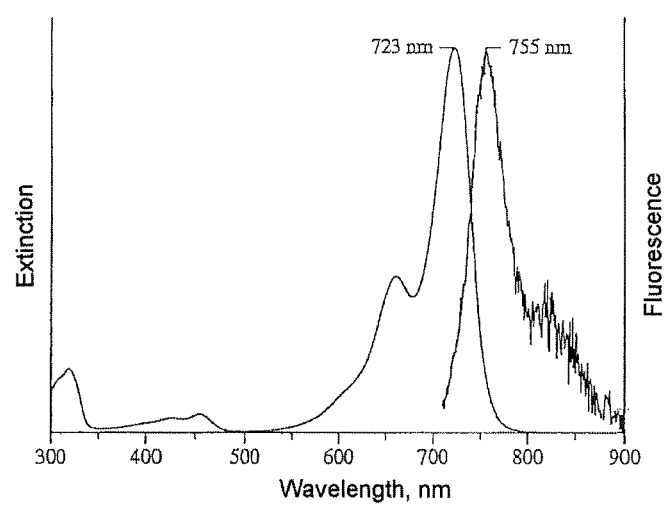
Figure 12:
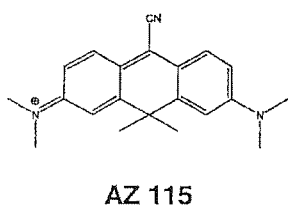
FIG. 12: Absorption and fluorescence spectrum of polycyclic compound 30 (AZ 115) in ethanol.
Figure 12:
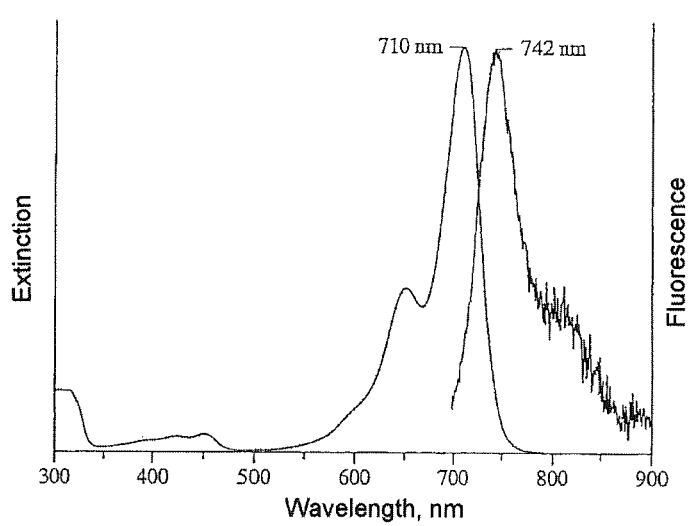
Figure 13:
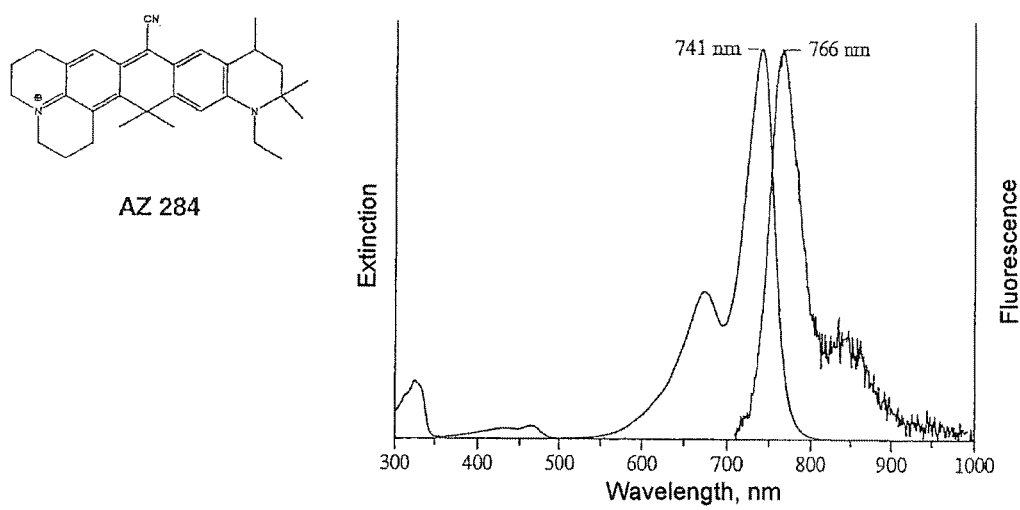
FIG. 13: Absorption and fluorescence spectrum of polycyclic compound 33 (AZ 284) in ethanol.
Figure 14:
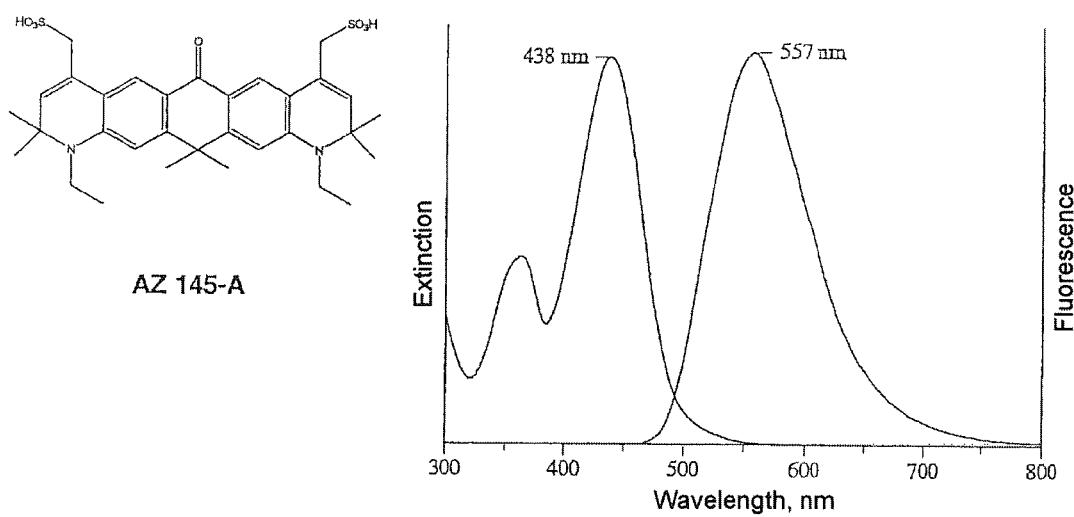
FIG. 14: Absorption and fluorescence spectrum of polycyclic compound 39 (AZ 145-A) in ethanol.
Figure 15:
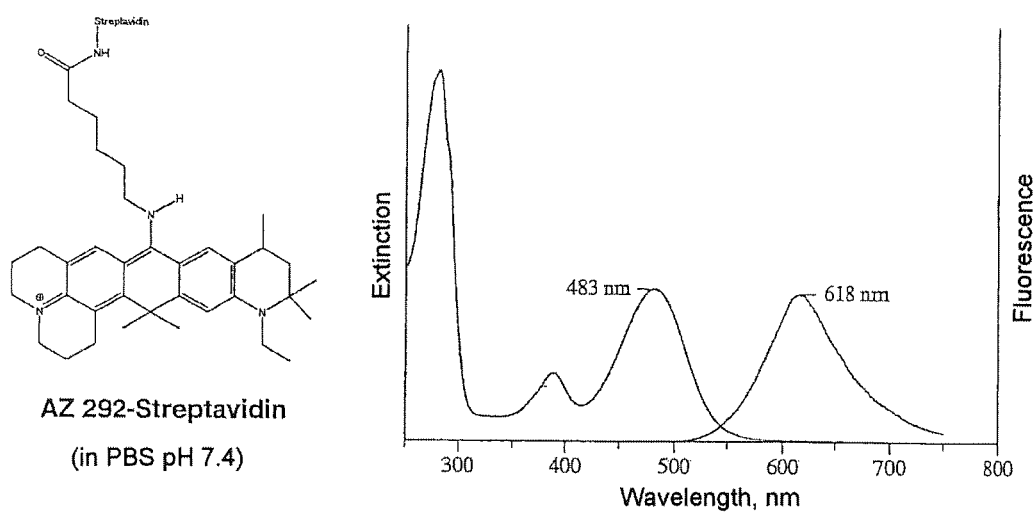
FIG. 15: Absorption and fluorescence spectrum of polycyclic compound 51 (AZ 292-streptavidin) in PBS.

A. Preparation of Polycyclic Precursor Compounds of the General Formula (III)

Compound 40 (AZ 151-A)

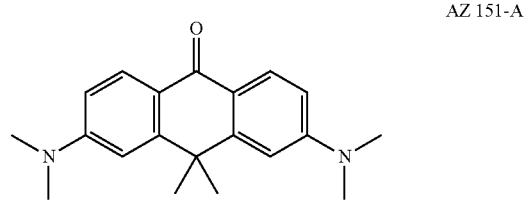

AZ 151-A

AZ 151 perchlorate (2.44 g, 6.21 mmol) is dissolved in 50 ml of acetone; finely powdered potassium permanganate (3.5 g, 22.15 mmol) is added in portions thereto, while cooling with ice, and stirring is then carried out for 18 hours. The mixture is filtered, the manganese dioxide that remains is washed several times with chloroform, and the combined organic phases are concentrated to dryness.

The residue is taken up in dichloromethane and purified by column chromatography on silica gel with dichloromethane/methanol (100:0-99:1). AZ 151-A (0.86 g, 2.79 mmol, 45%) is obtained in the form of a yellow crystalline solid (melting range 195-200° C.).

Optical properties in ethanol: $\lambda_{abs}$=394 nm; $\lambda_{fl}$=482 nm

B. Preparation of Polycyclic Precursor Compounds of the General Formula (II)

Compound 28 (AZ 111)

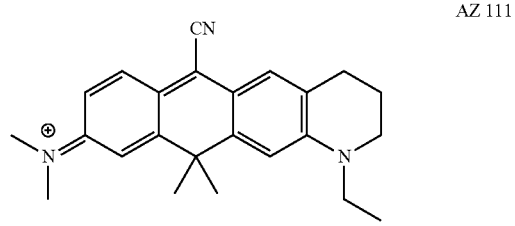 [SMILES: CCN1CCCc2cc3c(cc21)C(C)(C)C1=CC(=[N+](C)C)C=CC1=C3C#N]

AZ 111

AZ 110 perchlorate (250 mg, 0.58 mmol) is dissolved in 25 ml of dry acetonitrile and stirred for one hour in an $N_2$ stream. 10 ml of tetrabutylammonium cyanide in dry acetonitrile (310 mg, 1.16 mmol) are added and stirring is carried out for 2 hours at room temperature. The initially intense blue-coloured solution turns weak yellowish-green in colour.

For oxidation of the leuko compound, chloranil (170 mg, 0.69 mmol) is added and stirring is carried out under inert gas for a further 2 hours at room temperature. The reaction mixture spontaneously turns a deep green colour after addition of the oxidising agent. When the reaction is complete, concentration to dryness is carried out. The residue is taken up in chloroform/ethanol 98:2 and purified on silica gel with a gradient from chloroform to ethanol, the dye eluting with 5-15% ethanol.

The combined dye fractions are concentrated to dryness, taken up in 10 ml of ethanol and added dropwise to 150 ml of 5% sodium perchlorate solution. The precipitated dye is filtered off with suction and dried in vacuo over phosphorus pentoxide. AZ 111 (114 mg, 0.32 mmol, 55%) is obtained in the form of a crystalline green solid.

LC-MS: 358.2

Optical properties in ethanol: $\lambda_{abs}$=723 nm; $\lambda_{fl}$=755 nm

Compound 29 (AZ 112)

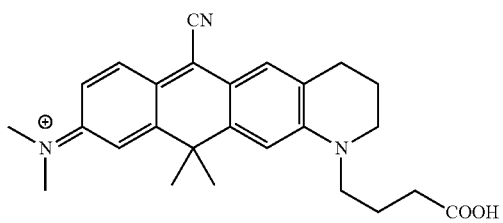

AZ 112

ATTO 610 perchlorate (250 mg, 0.51 mmol), a dye obtainable from ATTO-TEC GmbH, is dissolved in 25 ml of dry acetonitrile and stirred for one hour in an $N_2$ stream. 10 ml of tetrabutylammonium cyanide (273 mg, 1.02 mmol) in dry acetonitrile are added and stirring is carried out for 2 hours at room temperature. The initially intense blue-coloured solution turns weak yellowish-green in colour.

For oxidation of the leuko compound, chloranil (170 mg, 0.69 mmol) is added and stirring is carried out under inert gas for a further 2 hours at room temperature. The reaction mixture spontaneously turns a deep green colour after addition of the oxidising agent. When the reaction is complete, concentration to dryness is carried out. The residue is taken up in chloroform/ethanol 95:5 and purified on silica gel with a gradient from chloroform to ethanol, the dye eluting with 10-20% ethanol.

The combined dye fractions are concentrated to dryness, taken up in 10 ml of ethanol and added dropwise to 150 ml of 5% sodium perchlorate solution. The precipitated dye is filtered off with suction and dried in vacuo over phosphorus pentoxide. AZ 112 (116 mg, 0.29 mmol, 55%) is obtained in the form of a crystalline green solid.

LC-MS: 416.2

Optical properties in ethanol: $\lambda_{abs}$=726 nm; $\lambda_{fl}$=754 nm

Compound 32 (AZ 147)

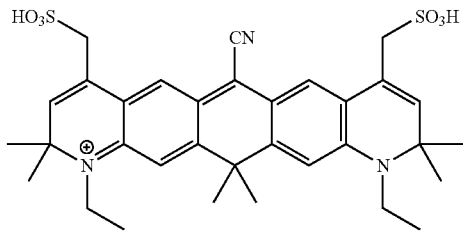

AZ 147

AZ 145 sodium salt (200 mg, 0.26 mmol) is dissolved in 8 ml of dry dimethylformamide and stirred for 30 minutes in an $N_2$ stream. 10 ml of tetrabutylammonium cyanide (213 mg, 0.79 mmol) in dry dimethylformamide are added and stirring is carried out for 2 hours at room temperature. The initially intense blue-coloured solution turns weak yellowish-green in colour.

For oxidation of the leuko compound, chloranil (78 mg, 0.32 mmol) is added and stirring is carried out under inert gas for a further 2 hours at room temperature. The reaction mixture gradually turns a deep green colour after addition of the oxidising agent. When the reaction is complete, concentration to dryness is carried out. The residue is taken up in chloroform/ethanol 85:15 and purified on silica gel with a gradient from chloroform to ethanol, the dye eluting with 40-50% ethanol.

The combined dye fractions are concentrated to dryness. The residue is taken up in a small amount of ethanol and added dropwise to 100 ml of diethyl ether. The precipitated dye is filtered off with suction and dried in vacuo over phosphorus pentoxide. AZ 147 (110 mg, 0.17 mmol, 65%) is obtained in the form of a crystalline green solid.

LC-MS: 638.3

Optical properties in ethanol: $\lambda_{abs}$=801 nm; $\lambda_{fl}$=830 nm

Compound 33 (AZ 284)

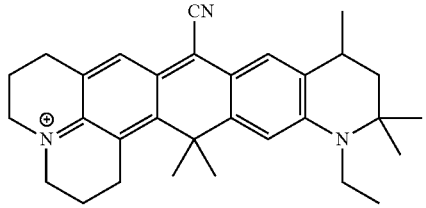

AZ 284

AZ 124 perchlorate (250 mg, 0.47 mmol) is dissolved in 25 ml of dry acetonitrile and stirred for one hour in an $N_2$ stream. 10 ml of tetrabutylammonium cyanide (255 mg, 0.95 mmol) in dry acetonitrile are added and stirring is carried out for 2 hours at room temperature. The initially intense blue-coloured solution turns weak yellowish-green in colour.

For oxidation of the leuko compound, chloranil (140 mg, 0.57 mmol) is added and stirring is carried out under inert gas for a further 2 hours at room temperature. The reaction mixture spontaneously turns a deep green colour after addition of the oxidising agent. When the reaction is complete, concentration to dryness is carried out. The residue is taken up in chloroform/ethanol 98:2 and purified on silica gel with a gradient from chloroform to ethanol, the dye eluting with 5-10% ethanol.

The combined dye fractions are concentrated to dryness, taken up in 10 ml of ethanol and added dropwise to 150 ml of 5% sodium perchlorate solution. The precipitated dye is filtered off with suction and dried in vacuo over phosphorus pentoxide. AZ 284 (137 mg, 0.30 mmol, 64%) is obtained in the form of a crystalline green solid.

LC-MS: 452.3

Optical properties in ethanol: $\lambda_{abs}$=741 nm; $\lambda_{fl}$=766 nm

C. Preparation of Polycyclic Compounds of the General Formula (I)

Compound 5 (AZ 286)

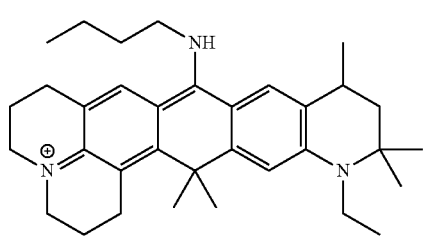

AZ 286

AZ 284 perchlorate (250 mg, 0.45 mmol) is dissolved in 40 ml of acetonitrile, and n-butylamine (166 mg, 2.26 mmol) is added thereto. The reaction mixture is stirred for 4 hours at room temperature, the solution turning yellowish-orange in colour and exhibiting an intense green fluorescence.

The reaction solution is concentrated to dryness, taken up in 15 ml of water/acetone/TFA in a ratio of 700/300/0.1, filtered (0.45 μm) and purified on silica gel RP 18 with a gradient from water to acetone.

The product fractions are combined; 5 ml of 10% sodium perchlorate solution are added thereto, and concentration is carried out in a rotary evaporator. The dye that precipitates is filtered off with suction and dried in vacuo over phosphorus pentoxide. AZ 286 (238 mg, 0.40 mmol, 88%) is obtained in the form of an orange-coloured crystalline solid.

LC-MS: 338.3

Optical properties in ethanol: $\lambda_{abs}$=480 nm, $\lambda_{fl}$=601 nm, $\eta_{fl}$=79%

Compound 7 (AZ 292)

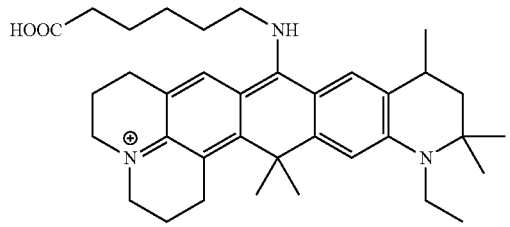

AZ 292

AZ 284 perchlorate (190 mg, 0.34 mmol) is dissolved in 6 ml of DMSO, and 350l of a 2M solution of 6-aminohexanoic acid potassium salt (203 mg, 1.20 mmol) in water are added thereto. The reaction mixture spontaneously changes colour from green to deep brownish-red.

Stirring is carried out for one hour at room temperature. 17 ml of water/acetone/TFA in a ratio of 800/200/0.1 are added to the reaction solution, which is filtered (0.45 μm) and purified on silica gel RP 18 with a gradient from water to acetone.

The product fractions are combined; 5 ml of 10% sodium perchlorate solution are added thereto, and concentration is carried out in a rotary evaporator. The dye that precipitates is filtered off with suction and dried in vacuo over phosphorus pentoxide. AZ 292 (165 mg, 0.25 mmol, 77%) is obtained in the form of an orange-coloured crystalline solid.

LC-MS: 556.4

Optical properties in ethanol: $\lambda_{abs}$=480 nm, $\lambda_{fl}$=601 nm, $\eta_{fl}$=78%

Compound 8 (AZ 312)

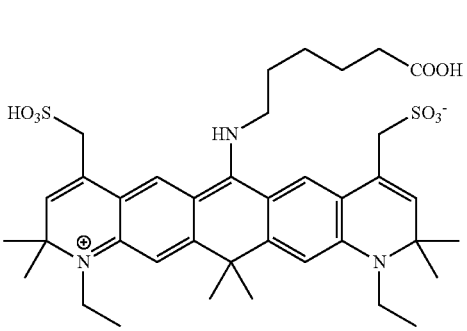

AZ 312

AZ 147 sodium salt (110 mg, 0.638 mmol) is dissolved in 5 ml of DMSO, and 200l of a 2M solution of 6-aminohexanoic acid potassium salt (68 mg, 0.40 mmol) in water are added thereto. The reaction mixture spontaneously changes colour from greenish-yellow to deep brownish-red.

Stirring is carried out for one hour at room temperature. 18 ml of water/acetone/TFA in a ratio of 950:50:0.1 are added, and filtration is carried out (0.45 μm). The filtrate is purified on silica gel RP18 with a gradient from water to acetone, the product eluting with water/acetone/rFA in a ratio of 700:300:0.1.

The product fractions are concentrated to dryness. AZ 312 (88 mg, 0.12 mmol, 69%) is obtained in the form of an orange-red crystalline solid.

LC-MS: 742.3

Optical properties in ethanol: $\lambda_{abs}$=491 nm, $\lambda_{fl}$=651 nm, $\eta_{fl}$=61% Optical properties in PBS buffer pH 7.4: $\lambda_{abs}$=490 nm, $\lambda_{fl}$=670 nm, $\eta_{fl}$=26%

Compound 14 (AZ 327)

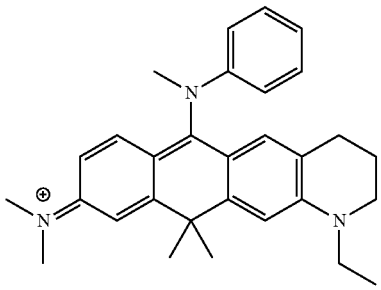

AZ 327

AZ 110-A (60 mg, 0.17 mmol) is dissolved in 4 ml of dichloromethane, and trifluoromethanesulfonic anhydride (145 μl, 0.86 mmol) is added dropwise thereto. The solution, which is initially deep blue and later bluish-green in colour, is stirred for 10 minutes at 25° C. N-Methylaniline (186 mg, 1.72 mmol) is added dropwise, and stirring is carried out for 3 hours at 25° C.

The reaction solution is concentrated to dryness, and the residue is taken up in 12 ml of water/acetone/TFA in a ratio of 600:400:0.1, filtered (0.45 gpm) and purified on silica gel RP18 with a gradient from water to acetone, the dye eluting at 400:600:0.1.

The product fractions are combined; 5 ml of 10% sodium perchlorate solution are added thereto, and concentration is carried out in a rotary evaporator. The dye that precipitates is filtered off with suction and dried in vacuo over phosphorus pentoxide. AZ 327 (79 mg, 0.15 mmol, 85%) is obtained in the form of a blue crystalline solid.

LC-MS: 438.2

Optical properties in acetonitrile: $\lambda_{abs}$=629 nm, $\eta_{fl}$<0.1%

Compound 15 (AZ 329)

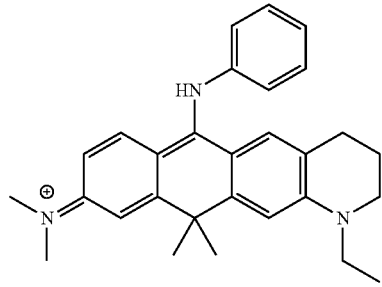

AZ 329

AZ 110-A (60 mg, 0.17 mmol) is dissolved in 4 ml of dichloromethane, and trifluoromethanesulfonic anhydride (145 µl, 0.86 mmol) is added dropwise thereto. The solution, which is initially deep blue and later bluish-green in colour, is stirred for 10 minutes at 25° C. Aniline (157 µl, 1.72 mmol) is added dropwise, and stirring is carried out for minutes at 25° C.

The reaction solution is concentrated to dryness, and the residue is taken up in 12 ml of water/acetone/TFA in a ratio of 700:300:0.1, filtered (0.45 µm) and purified on silica gel RP18 with a gradient from water to acetone, the dye eluting at 500:500:0.1.

The product fractions are combined; 5 ml of 10% sodium perchlorate solution are added thereto, and concentration is carried out in a rotary evaporator. The dye that precipitates is filtered off with suction and dried in vacuo over phosphorus pentoxide. AZ 329 (61 mg, 0.12 mmol, 68%) is obtained in the form of a dark-red crystalline solid.

LC-MS: 424.2

Optical properties in ethanol: $\lambda_{abs}$=507 nm, $\lambda_{fl}$=620 nm, $\eta_{fl}$<1%

Compound 21 (AZ 277)

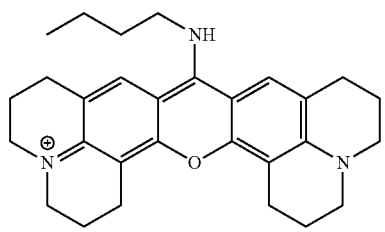

AZ 277

Rhodamine 800 perchlorate (60 mg, 0.12 mmol) is dissolved in 15 ml of acetonitrile, and n-butylamine (44 mg, 0.61 mmol) is added thereto. The reaction mixture is stirred for 2 hours at room temperature, the solution turning yellowish-orange in colour and exhibiting an intense green fluorescence.

The reaction solution is concentrated to dryness, taken up in 15 ml of water/acetone/TFA in a ratio of 600/400/0.1, filtered (0.45 µm) and purified on silica gel RP 18 with a gradient from water to acetone.

The product fractions are combined; 5 ml of 10% sodium perchlorate solution are added thereto, and concentration is carried out in a rotary evaporator. The dye that precipitates is filtered off with suction and dried in vacuo over phosphorus pentoxide. AZ 277 (54 mg, 0.10 mmol, 82%) is obtained in the form of a yellow crystalline solid.

LC-MS: 442.3

Optical properties in ethanol: $\lambda_{abs}$=456 nm, $\lambda_{fl}$=555 nm, $\eta_{fl}$=82%

Compound 22 (AZ 278)

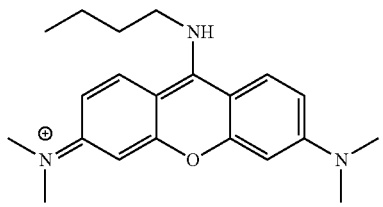

AZ 278

9-Cyanotetramethylpyronine perchlorate (250 mg, 0.64 mmol) is dissolved in 40 ml of acetonitrile, and n-butylamine (233 mg, 3.19 mmol) is added thereto. The reaction mixture is stirred for 2 hours at room temperature, the solution turning yellowish-orange in colour and exhibiting an intense green fluorescence.

The reaction solution is concentrated to dryness, taken up in 15 ml of water/acetone/TFA in a ratio of 700/300/0.1, filtered (0.45 µm) and purified on silica gel RP 18 with a gradient from water to acetone.

The product fractions are combined; 5 ml of 10% sodium perchlorate solution are added thereto, and concentration is carried out in a rotary evaporator. The dye that precipitates is filtered off with suction and dried in vacuo over phosphorus pentoxide. AZ 278 (225 mg, 0.51 mmol, 81%) is obtained in the form of a yellow crystalline solid.

LC-MS: 338.3

Optical properties in ethanol: $\lambda_{abs}$=433 nm, $\lambda_{fl}$=524 nm, $\eta_{fl}$=47%

The invention claimed is:

1. A polycyclic compound of the general formula (I)

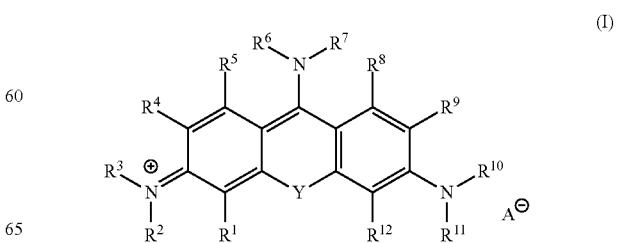

(I)

wherein $R^1$, $R^4$, $R^5$, $R^8$, $R^9$ and $R^{12}$ independently of one another denote hydrogen; halogen; CN; OH; O(alkyl); O(aryl); SH; S(alkyl); S(aryl); $NH_2$; NH(alkyl); NH(aryl); $N(alkyl)_2$; $N(aryl)_2$; $NO_2$; CHO; COOH; COO(alkyl); COO(aryl); $PO_3H_2$; $SO_3H$; a hydrocarbon group comprising from 1 to 20 carbon atoms; a hydrocarbon group comprising one or more heteroatoms selected from the group consisting of N, O and S; or a hydrocarbon group comprising one or more substituents selected from the group consisting of halogen, CN, OH, O(alkyl), O(aryl), SH, S(alkyl), S(aryl), $NH_2$, NH(alkyl), NH(aryl), $N(alkyl)_2$, $N(aryl)_2$, $NO_2$, CHO, COOH, COO(alkyl), COO(aryl), $PO_3H_2$ and $SO_3H$, $R^2$, $R^3$, $R^{10}$ and $R^{11}$ independently of one another denote hydrogen; a hydrocarbon group having from 1 to 20 carbon atoms; a hydrocarbon group comprising one or more heteroatoms selected from the group consisting of N, O and S; or a hydrocarbon group comprising one or more substituents selected from the group consisting of halogen, CN, OH, O(alkyl), O(aryl), SH, S(alkyl), S(aryl), $NH_2$, NH(alkyl), NH(aryl), $N(alkyl)_2$, $N(aryl)_2$, $NO_2$, CHO, COOH, COO(alkyl), COO(aryl), $PO_3H_2$ and $SO_3H$, $R^6$ and $R^7$ independently of one another denote hydrogen; $NR^{13}R^{14}$; a hydrocarbon group having from 1 to 20 carbon atoms; or an analyte molecule group, wherein $R^{13}$ and $R^{14}$ independently of one another denote hydrogen; halogen; CN; OH; O(alkyl); O(aryl); SH; S(alkyl); S(aryl); $NH_2$; NH(alkyl); NH(aryl); $N(alkyl)_2$; $N(aryl)_2$; $NO_2$; CHO; COOH; COO(alkyl); COO(aryl); $PO_3H_2$; $SO_3H$; a hydrocarbon group comprising from 1 to 20 carbon atoms; a hydrocarbon group comprising one or more heteroatoms selected from the group consisting of N, O and S; or a hydrocarbon group comprising one or more substituents selected from the group consisting of halogen, CN, OH, O(alkyl), O(aryl), SH, S(alkyl), S(aryl), $NH_2$, NH(alkyl), NH(aryl), $N(alkyl)_2$, $N(aryl)_2$, $NO_2$, CHO, COOH, COO(alkyl), COO(aryl), $PO_3H_2$ and $SO_3H$, wherein $R^6$ and $R^7$ do not simultaneously denote hydrogen, or wherein $R^6$ and $R^7$, together with the N atom to which they are attached, form a 3- to 7-membered ring;

a 3- to 7-membered ring comprising one or more double bonds or/and one or more additional heteroatoms selected from the group consisting of N, O and S; or a 3- to 7-membered ring comprising one or more substituents selected from the group consisting of halogen, CN, OH, O(alkyl), O(aryl), SH, S(alkyl), S(aryl), $NH_2$, NH(alkyl), NH(aryl), $N(alkyl)_2$, $N(aryl)_2$, $NO_2$, CHO, COOH, COO(alkyl), COO(aryl), $PO_3H_2$, $SO_3H$, a hydrocarbon group comprising from 1 to 20 carbon atoms, a hydrocarbon group fused with one or more 3- to 7-membered rings, a hydrocarbon group comprising one or more heteroatoms selected from the group consisting of N, O and S, and a hydrocarbon group comprising one or more substituents selected from the group consisting of halogen, CN, OH, O(alkyl), O(aryl), SH, S(alkyl), S(aryl), $NH_2$, NH(alkyl), NH(aryl), $N(alkyl)_2$, $N(aryl)_2$, $NO_2$, CHO, COOH, COO(alkyl), COO(aryl), $PO_3H_2$ and $SO_3H$, Y denotes a group selected from $CR^{15}R^{16}$, $NR^{17}$, O, S and Se, wherein $R^{15}$, $R^{16}$ and $R^{17}$ independently of one another denote hydrogen; CN; COOH; COO(alkyl); COO(aryl); $PO_3H_2$; $SO_3H$; a hydrocarbon group comprising from 1 to 20 carbon atoms; a hydrocarbon group comprising one or more heteroatoms selected from the group consisting of N, O and S; or a hydrocarbon group comprising one or more substituents selected from the group consisting of halogen, CN; OH, O(alkyl), O(aryl), SH, S(alkyl), S(aryl), $NH_2$, NH(alkyl), NH(aryl), $N(alkyl)_2$, $N(aryl)_2$, $NO_2$, CHO, COOH, COO(alkyl), COO(aryl), $PO_3H_2$ and $SO_3H$, or wherein $R^{15}$ and $R^{16}$, together with the carbon atom to which they are attached, form a 3- to 7-membered ring;

a 3- to 7-membered ring comprising one or more double bonds or/and one or more heteroatoms selected from the group consisting of N, O and S;

a 3- to 7-membered ring comprising one or more substituents selected from the group consisting of halogen, CN, OH, O(alkyl), O(aryl), SH, S(alkyl), S(aryl), $NH_2$, NH(alkyl), NH(aryl), $N(alkyl)_2$, $N(aryl)_2$, $NO_2$, CHO, COOH, COO(alkyl), COO(aryl), $PO_3H_2$, $SO_3H$, a hydrocarbon group having from 1 to 20 carbon atoms, a hydrocarbon group fused with one or more 3- to 7-membered rings, a hydrocarbon group comprising one or more heteroatoms selected from the group consisting of N, O and S, and a hydrocarbon group comprising one or more substituents selected from the group consisting of halogen, CN, OH, O(alkyl), O(aryl), SH, S(alkyl), S(aryl), $NH_2$, NH(alkyl), NH(aryl), $N(alkyl)_2$, $N(aryl)_2$, $NO_2$, CHO, COOH, COO(alkyl), COO(aryl), $PO_3H_2$ and $SO_3H$, and $A^-$ denotes an anion, or wherein $R^1$ and $R^2$, $R^3$ and $R^4$, $R^9$ and $R^{10}$ or/and $R^{11}$ and $R^{12}$, together with the atoms to which they are attached, form a 5- or 6-membered ring; or a 5- or 6-membered ring comprising one or more double bonds or/and one or more substituents selected from the group consisting of halogen, CN, OH, O(alkyl), O(aryl), SH, S(alkyl), S(aryl), $NH_2$, NH(alkyl), NH(aryl), $N(alkyl)_2$, $N(aryl)_2$, $NO_2$, CHO, COOH, COO(alkyl), COO(aryl), $PO_3H_2$, $SO_3H$, a hydrocarbon group comprising from 1 to 20 carbon atoms, a hydrocarbon group comprising one or more heteroatoms selected from the group consisting of N, O and S, and a hydrocarbon group comprising one or more substituents selected from the group consisting of halogen, CN, OH, O(alkyl), O(aryl), SH, S(alkyl), S(aryl), $NH_2$, NH(alkyl), NH(aryl), $N(alkyl)_2$, $N(aryl)_2$, $NO_2$, CHO, COOH, COO(alkyl), COO(aryl), $PO_3H_2$ and $SO_3H$, wherein $R^2$ and $R^3$ or $R^{10}$ and $R^{11}$, together with the atoms to which they are attached, do not combine to form a 6-membered ring.

2. The polycyclic compound of claim 1, wherein $R^1$ and $R^2$, $R^3$ and $R^4$, $R^9$ and $R^{10}$ or/and $R^{11}$ and $R^{12}$, together with the atoms to which they are attached, form a 5- or 6-membered ring.

3. The polycyclic compound of claim 2, wherein at least one 5- or 6-membered ring is substituted by one or more hydrocarbon groups having from 1 to 20 carbon atoms or one or more hydrocarbon groups comprising one or more substituents selected from the group consisting of COOH, COO(alkyl), COO(aryl) and SO$_3$H.

4. The polycyclic compound of claim 1, wherein R$^2$, R$^3$, R$^{10}$ or/and R$^{11}$ denotes a hydrocarbon group having from 1 to 20 carbon atoms.

5. The polycyclic compound of claim 1, wherein at least two radicals selected from the group consisting of R$^5$, R$^8$ and R$^{12}$, denote hydrogen.

6. The polycyclic compound of claim 1, wherein R$^6$ and R$^7$ independently of one another denote hydrogen; a hydrocarbon group having from 1 to 20 carbon atoms; a hydrocarbon group comprising one or more heteroatoms selected from the group consisting of N, O and S; or a hydrocarbon group comprising one or more substituents selected from the group consisting of halogen, OH, SH, NH$_2$, COOH, COO(alkyl), COO(aryl) and SO$_3$H.

7. The polycyclic compound of claim 1, wherein Y denotes a group selected from CR$^{15}$R$^{16}$, O and S, wherein R$^{15}$ and R$^{16}$ independently of one another denote a hydrocarbon group having from 1 to 20 carbon atoms.

8. A method for making the polycyclic compound of general formula (I) comprising reacting a polycyclic precursor compound of the general formula (II)

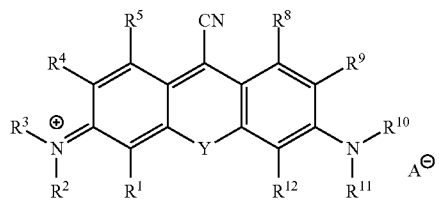
(II)

with a primary or secondary amine of the general formula HNR$^6$R$^7$, wherein R$^2$, R$^3$, R$^4$, R$^5$, R$^6$, R$^7$, R$^8$, R$^9$, R$^{10}$, R$^{11}$, R$^{12}$, Y and A$^-$ are as defined in claim 1.

9. A polycyclic precursor compound of the general formula (II)

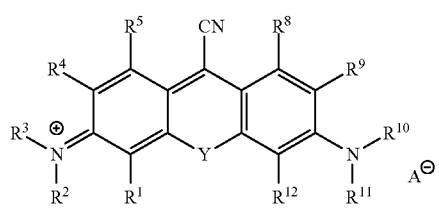
(II)

wherein R$^1$, R$^2$, R$^3$, R$^4$, R$^5$, R$^8$, R$^9$, R$^{10}$, R$^{11}$, R$^{12}$ and A$^-$ are as defined in claim 1, and Y denotes a group selected from CR$^{15}$R$^{16}$, S and Se, wherein R$^{15}$ and R$^{16}$ are as defined in claim 1.

10. A method for making the polycyclic precursor compound of the general formula (II) comprising reacting a polycyclic precursor compound of the general formula (IV)

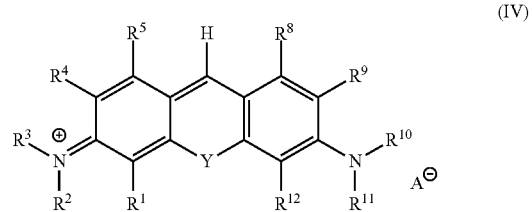
(IV)

with a tetraalkylammonium cyanide of the general formula N(alkyl)$_4$CN and an oxidising agent, wherein R$^1$, R$^2$, R$^3$, R$^4$, R$^5$, R$^8$, R$^9$, R$^{10}$, R$^{11}$, R$^{12}$ and Y are as defined in claim 1.

11. The method of claim 8, wherein the reaction is carried out at a temperature of at least 0° C.

12. The method of claim 10, wherein the reaction is carried out at a temperature of at least 0° C.

13. The method of claim 8, wherein the reaction is carried out in the presence of a solvent.

14. The method of claim 10, wherein the reaction is carried out in the presence of a solvent.

15. A polycyclic precursor compound of the general formula (III)

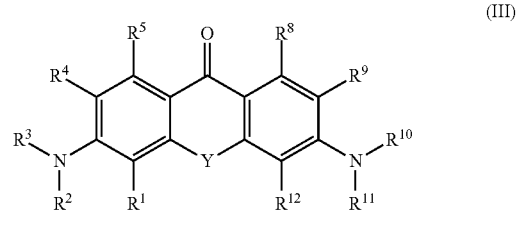
(III)

wherein R$^1$, R$^2$, R$^3$, R$^4$, R$^5$, R$^8$, R$^9$, R$^{10}$, R$^{11}$, R$^{12}$ and Y are as defined in claim 1.

16. A method for the preparation of the polycyclic precursor compound of the general formula (III) comprising reacting a polycyclic precursor compound of the general formula (IV)

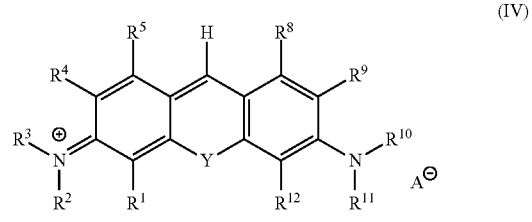
(IV)

with an oxidising agent, wherein R$^1$, R$^2$, R$^3$, R$^4$, R$^5$, R$^8$, R$^9$, R$^{10}$, R$^{11}$, R$^{12}$, Y and A$^-$ are as defined in claim 1.

17. A method for the qualitative or/and quantitative determination of an analyte in a sample comprising bonding the polycyclic compound of claim 1 to the analyte.

18. A method for the qualitative or/and quantitative determination of an analyte in a sample comprising bonding the polycyclic precursor compound of claim 15 to the analyte.

19. The method of claim 17, wherein determining the analyte comprises labelling of the analyte by covalent bonding of the polycyclic compound to the analyte.

20. The method of claim 18, wherein determining the analyte comprises labelling of the analyte by covalent bonding of the polycyclic precursor compound to the analyte.

21. The method of claim 17, wherein the analyte is a biomolecule.

22. The method of claim 18, wherein the analyte is a biomolecule, in particular a peptide, a polypeptide, a protein, a nucleotide, a polynucleotide, a nucleoside, a nucleic acid, a nucleic acid analogue or a hapten.

23. A method for the qualitative or/and quantitative determination of an analyte in a sample comprising bonding the polycyclic precursor compound of claim 9 to the analyte.

24. The method of claim 23, wherein determining the analyte comprises labelling of the analyte by covalent bonding of the polycyclic precursor compound to the analyte.

25. The method of claim 23, wherein the analyte is a biomolecule.

26. The polycyclic compound of claim 1, wherein $R^2$, $R^3$, $R^{10}$ or/and denotes an alkyl group having from 1 to 6 carbon atoms.

27. The polycyclic compound of claim 1, wherein $R^5$ and $R^8$ denote hydrogen.

28. The polycyclic compound of claim 1, wherein Y denotes a group selected from $CR^{15}R^{16}$, O and S, wherein $R^{15}$ and $R^{16}$ independently of one another denote an alkyl group having from 1 to 6 carbon atoms.

29. The method of claim 8, wherein the reaction is carried out at a temperature in the range of from 15° C. to 35° C.

30. The method of claim 10, wherein the reaction is carried out at a temperature in the range of from 15° C. to 35° C.

31. The method of claim 8, wherein the reaction is carried out in the presence of a solvent selected from the group consisting of acetone, acetonitrile, chloroform, dichloromethane, dimethyl sulfoxide, N,N-dimethylformamide and mixtures thereof.

32. The method of claim 10, wherein the reaction is carried out in the presence of a solvent selected from the group consisting of acetone, acetonitrile, chloroform, dichloromethane, dimethyl sulfoxide, N,N-dimethylformamide and mixtures thereof.

33. The method of claim 17, wherein the analyte is a peptide, a polypeptide, a protein, a nucleotide, a polynucleotide, a nucleoside, a nucleic acid, a nucleic acid analogue or a hapten.

34. The method of claim 23, wherein the analyte is a peptide, a polypeptide, a protein, a nucleotide, a polynucleotide, a nucleoside, a nucleic acid, a nucleic acid analogue or a hapten.

* * * * *